(12) United States Patent
Schmitz et al.

(10) Patent No.: US 8,062,300 B2
(45) Date of Patent: Nov. 22, 2011

(54) TISSUE REMOVAL WITH AT LEAST PARTIALLY FLEXIBLE DEVICES

(75) Inventors: Gregory P. Schmitz, Los Gatos, CA (US); Jeffrey L. Bleich, Palo Alto, CA (US); Steven A. Spisak, San Jose, CA (US); Roy Leguidleguid, Union City, CA (US); Jefferey Bleam, Boulder Creek, CA (US)

(73) Assignee: Baxano, Inc., San Jose, CA (US)

( * ) Notice: Subject to any disclaimer, the term of this patent is extended or adjusted under 35 U.S.C. 154(b) by 690 days.

(21) Appl. No.: 11/687,548

(22) Filed: Mar. 16, 2007

(65) Prior Publication Data

US 2007/0260252 A1 Nov. 8, 2007

Related U.S. Application Data

(63) Continuation-in-part of application No. 11/429,377, filed on May 4, 2006.

(60) Provisional application No. 60/869,070, filed on Dec. 7, 2006.

(51) Int. Cl.
*A61B 17/00* (2006.01)

(52) U.S. Cl. ........................................................ 606/85

(58) Field of Classification Search ............... 606/79, 606/82, 85
See application file for complete search history.

(56) References Cited

U.S. PATENT DOCUMENTS

| | | |
|---|---|---|
| 184,804 A | 11/1876 | Stohlmann |
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |

(Continued)

FOREIGN PATENT DOCUMENTS

DE 3209403 A1 9/1983

(Continued)

OTHER PUBLICATIONS

Tomita, et al. The Threadwire Saw: a New Device for Cutting Bone. J Bone Joint Surg Am. 78:1915-7, 1996.*

(Continued)

*Primary Examiner* — Thomas C. Barrett
*Assistant Examiner* — David Bates
(74) *Attorney, Agent, or Firm* — Shay Glenn LLP

(57) ABSTRACT

A device for modifying tissue in a patient may include: an elongate body having a rigid proximal portion and a flexible distal portion having first and second major surfaces; a proximal handle coupled with the proximal portion of the body; one or more tissue modifying members disposed along the first major surface of the distal portion of the body; a guidewire coupled with and extending from the distal portion of the body; and a distal handle removably couplable with the guidewire outside the patient.

50 Claims, 23 Drawing Sheets

U.S. PATENT DOCUMENTS

| | | |
|---|---|---|
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A * | 12/1993 | Foerster et al. ............... 600/585 |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |

| | | | | | | |
|---|---|---|---|---|---|---|
| 5,807,263 A | 9/1998 | Chance | | 6,360,750 B1 | 3/2002 | Gerber et al. |
| 5,810,744 A | 9/1998 | Chu et al. | | 6,364,886 B1 | 4/2002 | Sklar |
| 5,813,405 A | 9/1998 | Montano, Jr. et al. | | 6,368,324 B1 | 4/2002 | Dinger et al. |
| 5,824,040 A | 10/1998 | Cox et al. | | 6,370,411 B1 | 4/2002 | Osadchy et al. |
| 5,830,151 A | 11/1998 | Hadzic et al. | | 6,370,435 B2 | 4/2002 | Panescu et al. |
| 5,830,157 A | 11/1998 | Foote | | 6,383,509 B1 | 5/2002 | Donovan et al. |
| 5,830,188 A | 11/1998 | Abouleish | | 6,390,906 B1 | 5/2002 | Subramanian |
| 5,833,692 A * | 11/1998 | Cesarini et al. ............ 606/79 | | 6,391,028 B1 | 5/2002 | Fanton et al. |
| 5,836,948 A | 11/1998 | Zucherman et al. | | 6,416,505 B1 | 7/2002 | Fleischman et al. |
| 5,843,110 A | 12/1998 | Dross et al. | | 6,423,071 B1 | 7/2002 | Lawson |
| 5,846,196 A | 12/1998 | Siekmeyer et al. | | 6,423,080 B1 * | 7/2002 | Gellman et al. ............ 606/148 |
| 5,846,244 A | 12/1998 | Cripe | | 6,425,859 B1 | 7/2002 | Foley et al. |
| 5,851,191 A | 12/1998 | Gozani | | 6,425,887 B1 | 7/2002 | McGuckin et al. |
| 5,851,209 A | 12/1998 | Kummer et al. | | 6,436,101 B1 | 8/2002 | Hamada |
| 5,851,214 A | 12/1998 | Larsen et al. | | 6,442,848 B1 | 9/2002 | Dean |
| 5,853,373 A | 12/1998 | Griffith et al. | | 6,446,621 B1 | 9/2002 | Svensson |
| 5,865,844 A | 2/1999 | Plaia et al. | | 6,451,335 B1 | 9/2002 | Goldenheim et al. |
| 5,868,767 A | 2/1999 | Farley et al. | | 6,454,767 B2 | 9/2002 | Alleyne |
| 5,879,353 A | 3/1999 | Terry | | 6,464,682 B1 | 10/2002 | Snoke |
| 5,885,219 A | 3/1999 | Nightengale | | 6,466,817 B1 | 10/2002 | Kaula et al. |
| 5,895,417 A | 4/1999 | Pomeranz et al. | | 6,468,289 B1 | 10/2002 | Bonutti |
| 5,897,583 A | 4/1999 | Meyer et al. | | 6,470,209 B2 | 10/2002 | Snoke |
| 5,899,909 A | 5/1999 | Claren et al. | | 6,478,805 B1 | 11/2002 | Marino et al. |
| 5,904,657 A | 5/1999 | Unsworth et al. | | 6,487,439 B1 | 11/2002 | Skladnev et al. |
| 5,916,173 A | 6/1999 | Kirsner | | 6,488,636 B2 | 12/2002 | Bryan et al. |
| 5,918,604 A | 7/1999 | Whelan | | 6,491,646 B1 | 12/2002 | Blackledge |
| 5,919,190 A | 7/1999 | VanDusseldorp | | 6,500,128 B2 | 12/2002 | Marino |
| 5,928,158 A | 7/1999 | Aristides | | 6,500,189 B1 | 12/2002 | Lang et al. |
| 5,928,159 A | 7/1999 | Eggers et al. | | 6,512,958 B1 | 1/2003 | Swoyer et al. |
| 5,941,822 A | 8/1999 | Skladnev et al. | | 6,516,223 B2 | 2/2003 | Hofmann |
| 5,961,522 A | 10/1999 | Mehdizadeh | | 6,520,907 B1 | 2/2003 | Foley et al. |
| 5,972,013 A | 10/1999 | Schmidt | | 6,527,786 B1 | 3/2003 | Davis et al. |
| 5,976,110 A | 11/1999 | Greengrass et al. | | 6,533,749 B1 | 3/2003 | Mitusina et al. |
| 5,976,146 A | 11/1999 | Ogawa et al. | | 6,535,759 B1 | 3/2003 | Epstein et al. |
| 6,002,964 A | 12/1999 | Feler et al. | | 6,540,742 B1 | 4/2003 | Thomas et al. |
| 6,004,326 A | 12/1999 | Castro et al. | | 6,540,761 B2 | 4/2003 | Houser |
| 6,010,493 A | 1/2000 | Snoke | | 6,546,270 B1 | 4/2003 | Goldin et al. |
| 6,015,406 A | 1/2000 | Goble et al. | | 6,558,353 B2 | 5/2003 | Zohmann |
| 6,022,362 A | 2/2000 | Lee et al. | | 6,562,033 B2 | 5/2003 | Shah et al. |
| 6,030,383 A | 2/2000 | Benderev | | 6,564,078 B1 | 5/2003 | Marino et al. |
| 6,030,401 A | 2/2000 | Marino | | 6,564,079 B1 | 5/2003 | Cory et al. |
| 6,038,480 A | 3/2000 | Hrdlicka et al. | | 6,564,088 B1 | 5/2003 | Soller et al. |
| 6,048,345 A | 4/2000 | Berke et al. | | 6,569,160 B1 | 5/2003 | Goldin et al. |
| 6,068,642 A | 5/2000 | Johnson et al. | | 6,575,979 B1 | 6/2003 | Cragg |
| 6,073,051 A | 6/2000 | Sharkey et al. | | 6,579,291 B1 | 6/2003 | Keith et al. |
| 6,099,514 A | 8/2000 | Sharkey et al. | | 6,584,345 B2 | 6/2003 | Govari |
| 6,102,930 A | 8/2000 | Simmons, Jr. | | 6,592,559 B1 | 7/2003 | Pakter et al. |
| 6,106,558 A | 8/2000 | Picha | | 6,595,932 B2 | 7/2003 | Ferrera |
| 6,113,534 A | 9/2000 | Koros et al. | | 6,597,955 B2 | 7/2003 | Panescu et al. |
| D432,384 S | 10/2000 | Simons | | 6,606,523 B1 | 8/2003 | Jenkins |
| 6,132,387 A | 10/2000 | Gozani et al. | | 6,607,530 B1 | 8/2003 | Carl et al. |
| 6,136,014 A | 10/2000 | Sirimanne et al. | | 6,609,018 B2 | 8/2003 | Cory et al. |
| 6,142,993 A | 11/2000 | Whayne et al. | | 6,610,066 B2 | 8/2003 | Dinger et al. |
| 6,142,994 A | 11/2000 | Swanson et al. | | 6,620,129 B2 | 9/2003 | Stecker et al. |
| 6,146,380 A | 11/2000 | Racz et al. | | 6,622,731 B2 | 9/2003 | Daniel et al. |
| 6,152,894 A | 11/2000 | Kubler | | 6,624,510 B1 | 9/2003 | Chan et al. |
| 6,169,916 B1 | 1/2001 | West | | 6,626,916 B1 | 9/2003 | Yeung et al. |
| 6,205,360 B1 | 3/2001 | Carter et al. | | 6,632,184 B1 | 10/2003 | Truwit |
| 6,214,001 B1 | 4/2001 | Casscells et al. | | 6,638,233 B2 | 10/2003 | Corvi et al. |
| 6,214,016 B1 | 4/2001 | Williams et al. | | RE38,335 E | 11/2003 | Aust et al. |
| 6,236,892 B1 | 5/2001 | Feler | | 6,648,883 B2 | 11/2003 | Francischelli et al. |
| 6,251,115 B1 | 6/2001 | Williams et al. | | 6,666,874 B2 | 12/2003 | Heitzmann et al. |
| 6,256,540 B1 | 7/2001 | Panescu et al. | | 6,673,063 B2 | 1/2004 | Brett |
| 6,259,945 B1 | 7/2001 | Epstein et al. | | 6,673,068 B1 | 1/2004 | Berube |
| 6,261,582 B1 | 7/2001 | Needham et al. | | 6,678,552 B2 | 1/2004 | Pearlman |
| 6,266,551 B1 | 7/2001 | Osadchy et al. | | 6,682,535 B2 | 1/2004 | Hoogland |
| 6,266,558 B1 | 7/2001 | Gozani et al. | | 6,682,536 B2 | 1/2004 | Vardi et al. |
| 6,267,760 B1 | 7/2001 | Swanson | | 6,699,246 B2 | 3/2004 | Zucherman et al. |
| 6,272,367 B1 | 8/2001 | Chance | | 6,723,049 B2 | 4/2004 | Skladnev et al. |
| 6,277,094 B1 | 8/2001 | Schendel | | 6,726,531 B1 | 4/2004 | Harrel |
| 6,280,447 B1 | 8/2001 | Marino et al. | | 6,726,685 B2 | 4/2004 | To et al. |
| 6,292,702 B1 | 9/2001 | King et al. | | 6,733,496 B2 | 5/2004 | Ashley et al. |
| 6,298,256 B1 | 10/2001 | Meyer | | 6,736,835 B2 | 5/2004 | Pellegrino et al. |
| 6,312,392 B1 | 11/2001 | Herzon | | 6,746,451 B2 | 6/2004 | Middleton et al. |
| 6,324,418 B1 | 11/2001 | Crowley et al. | | 6,752,814 B2 | 6/2004 | Gellman et al. |
| 6,324,432 B1 | 11/2001 | Rigaux et al. | | 6,760,616 B2 | 7/2004 | Hoey et al. |
| 6,334,068 B1 | 12/2001 | Hacker | | 6,772,012 B2 | 8/2004 | Ricart et al. |
| 6,343,226 B1 | 1/2002 | Sunde et al. | | 6,776,765 B2 | 8/2004 | Soukup et al. |
| 6,358,254 B1 | 3/2002 | Anderson | | 6,788,966 B2 | 9/2004 | Kenan et al. |

| Patent Number | Date | Inventor(s) |
|---|---|---|
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 * | 3/2007 | Dekel ............................ 606/85 |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,216,001 B2 | 5/2007 | Hacker et al. |
| 7,223,278 B2 | 5/2007 | Davison et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0045937 A1 | 3/2003 | Ginn |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199166 A1 | 10/2004 | Schmieding et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |

| | | |
|---|---|---|
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0089650 A1 * | 4/2006 | Nolde ............... 606/85 |
| 2006/0089688 A1 | 4/2006 | Panescu |
| 2006/0094976 A1 | 5/2006 | Bleich |
| 2006/0095026 A1 | 5/2006 | Ricart et al. |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0206115 A1 | 9/2006 | Schomer et al. |
| 2006/0206117 A1 * | 9/2006 | Harp ............... 606/85 |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0258951 A1 | 11/2006 | Bleich et al. |
| 2006/0264952 A1 * | 11/2006 | Nelson et al. ............ 606/72 |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0086114 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0069709 A1 | 3/2009 | Schmitz et al. |
| 2009/0105604 A1 | 4/2009 | Bertagnoli et al. |
| 2009/0125036 A1 | 5/2009 | Bleich |
| 2009/0138056 A1 | 5/2009 | Anderson et al. |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177241 A1 | 7/2009 | Bleich et al. |
| 2009/0182382 A1 | 7/2009 | Justis et al. |
| 2009/0204119 A1 | 8/2009 | Bleich et al. |
| 2009/0209879 A1 | 8/2009 | Kaula et al. |
| 2010/0057087 A1 | 3/2010 | Cha |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0046613 A1 | 2/2011 | Schmitz et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0190772 A1 | 8/2011 | Saadat |
| 2011/0196257 A1 | 8/2011 | Schmitz et al. |

FOREIGN PATENT DOCUMENTS

| | | |
|---|---|---|
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |

| | | |
|---|---|---|
| EP | 1611851 A1 | 1/2006 |
| EP | 1006885 B1 | 9/2006 |
| FR | 2706309 | 12/1994 |
| JP | 2960140 B2 | 10/1999 |
| JP | 24065380 A2 | 3/2004 |
| RU | 2107459 | 3/1998 |
| WO | WO9734536 A2 | 9/1997 |
| WO | WO9918866 A1 | 4/1999 |
| WO | WO99/21500 A1 | 5/1999 |
| WO | WO00/67651 A1 | 11/2000 |
| WO | WO0108571 A1 | 2/2001 |
| WO | WO01/62168 A2 | 8/2001 |
| WO | WO0207901 A1 | 1/2002 |
| WO | WO0234120 A2 | 5/2002 |
| WO | WO02076311 A2 | 10/2002 |
| WO | WO03/026482 A2 | 4/2003 |
| WO | WO03/066147 A1 | 8/2003 |
| WO | WO2004002331 A1 | 1/2004 |
| WO | WO2004028351 A2 | 4/2004 |
| WO | WO2004/043272 A1 | 5/2004 |
| WO | WO2004056267 A1 | 7/2004 |
| WO | WO2004/078066 A2 | 9/2004 |
| WO | WO2004080316 A1 | 9/2004 |
| WO | WO2004096080 A2 | 11/2004 |
| WO | WO2005/009300 A1 | 2/2005 |
| WO | WO2005057467 A2 | 6/2005 |
| WO | WO2005077282 A1 | 8/2005 |
| WO | WO2005089433 A2 | 9/2005 |
| WO | WO2006009705 A2 | 1/2006 |
| WO | WO2006015302 A1 | 2/2006 |
| WO | WO2006017507 A2 | 2/2006 |
| WO | WO2006039279 A2 | 4/2006 |
| WO | WO2006042206 A2 | 4/2006 |
| WO | WO2006044727 A2 | 4/2006 |
| WO | WO2006047598 A1 | 5/2006 |
| WO | WO2006058079 A3 | 6/2006 |
| WO | WO2006058195 A2 | 6/2006 |
| WO | WO2006062555 A2 | 6/2006 |
| WO | WO2006086261 A1 | 8/2006 |
| WO | WO2006099285 A2 | 9/2006 |
| WO | WO2006102085 A2 | 9/2006 |
| WO | WO2007008709 A2 | 1/2007 |
| WO | WO2007021588 A1 | 2/2007 |
| WO | WO2007022194 A2 | 2/2007 |
| WO | WO2007059343 A2 | 2/2007 |
| WO | WO2007067632 A2 | 6/2007 |
| WO | WO2008008898 A2 | 1/2008 |

OTHER PUBLICATIONS

Schmitz et al.; U.S. Appl. No. 12/324,147 entitled "Tissue modification devices," filed Nov. 26, 2008.

Schmitz et al.; U.S. Appl. No. 12/352,385 entitled "Devices, methods and systems for neural localization," filed Jan. 12, 2009.

Bleich et al.; U.S. Appl. No. 12/352,978 entitled "Multiple pathways for spinal nerve rood decompression from a single access point," filed Jan. 13, 2009.

Bleich, Jeffrey; U.S. Appl. No. 12/357,289 entitled "Devices and methods for selective surgical removal of tissue," filed Jan. 21, 2009.

Barer Malvin, "Instrument to Enhance Passage of the Gigli Saw," Journal of Pediatric Orthopedics, Raven Press, New York, 1984, 4:762-763.

Baumgart et al., "Indikation and Technik der Knochendurchtrennung," Der Chirurg, 1998, vol. 69:1188-1196. (in German with Eng Summary).

Bohinski et al., "Novel use of a threadwire saw for high sacral amputation," Journal of neurosurgery: Spine, 2005, vol. 3, 71R78.

Brunori et al., "Celebrating the centennial (1894-1994): Leonardo Gigli and his wire saw," J. Neurosurg, 1995, 82:1086-1090.

Burrows, Harold, "Surgical instruments and appliances used in operations," Faber and Faber, London, 1937, total pp. 4.

Codman Laminectomy Shaver (a Johnson & Johnson company www.codman.com) catalogue, pp. 416-431, [online] Retrieved from the Internet: <URL: http:llwww.codman.com/PDFs/Catalog_04_R.pdf>.

Dammann, Gordon, Pictorial Encyclopedia of Civil War Medical Instruments and Equipment, Pictorial Histories Publishing Company, Missoula, Montana, 1983, Total pp. 2.

Edwards et al; "T-Saw Laminoplasty for the Management of Cervical Spondylotic Myelopathy," SPINE, Lippincott Williams & Wilkins, Inc., 2000, vol. 25 (14): 1788R1794.

Ellman Int. Disc-FX System Accessories K052241 [online] Retrieved from the Internet: <URL: http://www.ellman.com/medical/>.

Eralp et al., "A comparison of two osteotomy techniques for tibial lengthening," Archives of orthopaedic and trauma surgery, 2004, vol. 124:298R300.

Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet <http://www.aans.emedtrain.com/lumbar_stenosis/lumbarStenosis.swf>.

Fujita et al., "Chordoma in the Cervical Spine Managed with En Bloc Excision," SPINE, Lippincott Williams & Wilkins, Inc., 1999, 24 (17), 1848-1851.

Goel, Atul, "Neurosurgical forum, Supraorbital Craniotomy," Journal of Neurosurgery, 1994, vol. 81, 642-643.

Gore Smoother User Manual, W. L. Gore & Associates, Inc. Flagstaff, AZ, Dec. 1999,Total pp. 3.

Hara et al., "En Bloc Laminoplasty Performed with Threadwire Saw: Technical Note," Neurosurgery, Jan. 2001, vol. 48, No. 1, pp. 235-239.

Hata et al; "A less invasive surgery for rotator cuff tear: Mini-open repair," Journal of Shoulder and Elbow Surgery, 2001, vol. 10 No. 1, 11-16.

Honl et al; "The Use of Water-Jetting Technology in Prostheses Revision Surgery R First Results of Parameter Studies on Bone and Bone Cement," J. Biomed Mater Res (Applied Biomaterials), John Wiley & Sons, Inc, 2000, 53, 6: 781-790.

Integra Ruggles TM Kerrison Rongeurs [online] Retrieved from the Internet: <URL: http://www.integra-Is.com/products!?product=22>.

Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917R922.

Kawahara et al., "Recapping T-Saw Laminoplasty for Spinal Cord Tumors," SPINE, 1999, vol. 24 No. 13, pp. 1363-1370.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187RE190.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.

Mopec Bone-Cutting tool, Product brochure, Total pp. 4.

Nakagiri et al., "Thoracoscopic Rib Resection Using a Gigli Saw," The Annals of Thoracic Surgery, 2005, vol. 80, 755R756.

Osaka et al., "Clinical significance of a wide excision policy for sacrococcygeal chordoma," J Cancer Res Clin Oncol, 2005, Total pp. 6.

Paley et al., "Percutaneous Osteotomies," Orthopedic Clinics of North America, 1991, vol. 22 No. 4, 613-624.

Pancoast, Joseph, "A Treatise on Operative Surgery," Carey and Hart, Philadelphia,1844, Total pp. 11.

Park et al; "Cases of the Excision of Carious Joints," John Scrymgeour, Glasgow, 1806, Total pp. 6.

Peavy et al., "Comparison of Cortical Bone Ablations by Using Infrared Laser Wavelengths 2.9 to 9.2 µm, Lasers in Surgery and Medicine," 1999, vol. 26, 421R434.

Peltier, Leonard Orthopedics: A History and Iconography, Norman Publishing, San Francisco, 1993, Total pp. 3.

Reckling Frederick, "Modified Stethoscope Earpiece Makes Excellent Gigli Saw Guide," J Bone and Joint Surgery Am, Dec. 1972, 54-A(8), 1787-1788.

Rutkow, Ira, "Surgery an Illustrated History," Mosby'Year Book, Inc., St. Louis, 1993, Total pp. 4.

Schwieger et al., "Abrasive Water Jet Cutting as a New Procedure for Cutting Cancellous Bone'In Vitro Testing in Comparison with the Oscillating Saw," Wiley Interscience, www.interscience,wiley.com, Sep. 20, 2004, 223-228.

Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (In Russian w/ Eng Summary).

Shiraishi et al., "Results of Skip Laminectomy -Minimum 2-Year Follow-up Study Compared With Open-Door Laminoplasty," Spine, Lippincott Williams & Wilkins, Inc., 2003, vol. 28 No. 24, 2667-2672.

Shiraishi T., "A new technique for exposure of the cervical spine laminae," Journal of neurosurgery. Spine, 2002, vol. 96(1), 122-126.

Shiraishi T., Skip laminectomy—a new treatment for cervical spondylotic myelopathy, preserving bilateral muscular attachments to the spinous processes: a preliminary report, Spine, 2002, vol. 2(2), 108-115.

Skippen et al., "The Chain Saw R A Scottish Invention," Scottish Medical Journal, 2004, vol. 49(2), 72-75.

Stevens et al., "Calvarial Bone Graft Harvest Using the Gigli Saw," Journal of Oral and Maxillofacial Surgery, 1998, vol. 56, 798-799.

Takada et al., "Unusual Metastasis to the Cauda Equina From Renal Cell Carcinoma," SPINE, Lippincott Williams & Wilkins, Inc., 2003, vol. 28 No. 6, E114RE117.

Paktiss et al., "Afghan Percutaneous Osteotomy," Journal of Pediatric Orthopaedics, Raven Press Ltd, New York, 1993, vol. 13 No. 4, 531-533.

Tomita et al., "Expansive Midline T-Saw Laminoplasty (Modified Spinour Process-Splitting) for the Management of Cervical Myelopathy," SPINE, Lippincott Williams & Wilkins, Inc, 1998, 23(1), 32-37.

Tomita et al., "The Threadwire Saw: a New Device for Cutting Bone," The Journal of Bone and Joint Surgery, 1996, vol. 78, 1915-1917.

Tomita et al., "Total en bloc spondylectomy and circumspinal decompression for solitary spinal metastasis," Paraplegia, 1994, 32:36-46.

Tomita K. et al., "Total en bloc spondylectomy for solitary spinal metastases," International Orthopaedics (SICOT), 1994, 18: 291-298.

Truax, Charles, "The Mechanics of Surgery," Chicago, IL; 1899, Total pp. 3.

US Surgical Kerrison Spinal Rongeur K943116 [online] Retrieved from the internet: <URL: http://www.ussurg.com/uss/index.html>.

Wilkins, Robert H, "Neurosurgical Classics," Johnson Reprint Corporation, New York, 1965, 377-382.

Zeppelin Laminectomy Rongeur K901372, [online] Retrieved from the internet: <URL: http://www.zeppelin-medical.com/download/instruments.pdf>.

Bleich et al; U.S. Appl. No. 11/952,934 entitled "Tissue Removal Devices and Methods," filed Dec. 7, 2007.

Schmitz et al; U.S. Appl. No. 11/468,247 entitled "Tissue access guidewire system and method," filed Aug. 29, 2006.

Schmitz et al; U.S. Appl. No. 11/468,252 entitled "Tissue access guidewire system and method," filed Aug. 29, 2006.

Schmitz et al; U.S. Appl. No. 11/538,345 entitled "Articulating Tissue Cutting Device," filed Oct. 3, 2006.

Schmitz et al; U.S. Appl. No. 11/843,561 entitled "Surgical Probe and Method of Making," filed Aug. 22, 2007.

Schmitz et al; U.S. Appl. No. 11/870,370 entitled "Percutaneous Spinal Stenosis Treatment," filed Oct. 10, 2007.

Schmitz et al; U.S. Appl. No. 12/060,229 entitled "Method, system, and apparatus for neural localization," filed Mar. 31, 2008.

Tomita et al., "The Use of the T-Saw for Expansive Midline laminoplasty in the Treatment of Cervical Myelopathy," Orthopedics and Traumatology, No. 3, pp. 169-178, 2002.

Bleich, et al.; U.S. Appl. No. 12/127,535 entitled "Guidewire exchange systems to treat spinal stenosis," filed May 27, 2008.

Bleich, et al.; U.S. Appl. No. 12140,201 entitled "Devices and methods for measuring the space around a nerve root," filed Jun. 16, 2008.

Schmitz et al.; U.S. Appl. No. 12/170,392 entitled "Spinal access system and method," filed Jul. 9, 2008.

Bleich et al.; U.S. Appl. No. 12/428,369 entitled "Devices and methods for tissue modification," filed Apr. 22, 2009.

Bleich et al.; U.S. Appl. No. 12/504,545 entitled "Spinal access and neural localization," filed Jul. 16, 2009.

Schmitz et al.; U.S. Appl. No. 12/496,094 entitled "Access and tissue modification systems and methods," filed Jul. 1, 2009.

Arcenio et al.; U.S. Appl. No. 12/980,165 entitled "Systems and Methods for Performing Spinal Fusion", filed Dec. 28, 2010.

Bleich et al.; U.S. Appl. No. 12/984,162 entitled "Devices and Methods for Tissue Access", filed Jan. 4, 2011.

Schmitz et al.; U. S. Appl. No. 12/917,253; entitled "Tissue Access Guidewire System and Method"; filed Nov. 1, 2010.

Wallace et al.; U.S. Appl. No. 12/911,537 entitled "Devices and Methods for Treating Tissue", filed Oct. 25, 2010.

Wallace et al.; U.S. Appl. No. 13/007,381 entitled "Tissue Modification Devices", filed Jan. 14, 2011.

Saadat et al.; U.S. Appl. No. 13/078,376 entitled "Powered Tissue Modification Devices and Methods", filed Apr. 1, 2011.

US Surgical Kerrison Spinal Rongeur K943116 [online] Retrieved from the internet: <URL: http://www.ussurg com/uss/index.html>. Jul. 27, 1994.

Zeppelin Laminectomy Rongeur K901372, [online] Retrieved from the internet: <URL: http://www.zeppelin-medical.com/download/instruments.pdf>. Oct. 24, 2006.

Ellman Int. Disc-FX System Accessories K052241 [online] Retrieved from the Internet: <URL: http://www.ellman.com/ medical/>. Feb. 27, 2006.

Schwieger et al., "Abrasive Water Jet Cutting as a New Procedure for Cutting Cancellous Bone—In Vitro Testing in Comparison with the Oscillating Saw," Wiley Interscience, www.interscience,wiley.com, Sep. 20, 2004, 223-228. Sep. 20, 2004.

Mopec Bone-Cutting tool, Product brochure, Total pp. 4. First accessed Dec. 15, 2005.

Codman Laminectomy Shaver (a Johnson & Johnson company www. codman.com) catalogue, pp. 416-431, [online] Retrieved from the internet: <URL: http:llwww.codman.com/PDFs/Catalog_04_R. pdf >. First accessedOct. 24, 2006.

Integra Ruggles TM Kerrison Rongeurs [online] Retrieved from the internet: <URL: http://www.integra-is.com/products!? product=22>. First accessed Oct. 24, 2006.

Garabedian et al.; U.S. Appl. No. 12/824,043; entitled "Surgical Tools for Treatment of Spinal Stenosis"; filed Jun. 25, 2010.

Schmitz et al.; U.S. Appl. No. 12/816,729 entitled Access and Tissue Modification Systems and Methods, filed Jun. 16, 2010.

Wallace et al.; U.S. Appl. No. 12/724,315 entitled "Flexible Neural Localization Devices and Methods," filed Mar. 15, 2010.

Wallace et al.; U.S. Appl. No. 12/773,595 entitled "Tissue Modification Devices and Methods," filed May 4, 2010.

Bleich et al.; U.S. Appl. No. 12/637,447 entitled "Devices and methods for tissue modification," filed Dec. 14, 2009.

Bleich et al.; U.S. Appl. No. 13/112,886 entitled "Methods, Systems and Devices for Carpal Tunnel Release", filed May 20, 2011.

Bleich et al.; U.S. Appl. No. 13/112,918 entitled "Methods, Systems and Devices for Carpal Tunnel Release", filed May 20, 2011.

Herkowitz. , "The Cervical Spine Surgery Atlas", *Herkowitz, "The Cervical Spine Surgery Atlas"*, 2004, 2nd Edition Jan. 1, 2004 , 203-206, 208.

* cited by examiner

TISSUE REMOVAL WITH AT LEAST PARTIALLY FLEXIBLE DEVICES

CROSS-REFERENCES TO RELATED APPLICATIONS

The present application is a continuation-in-part of U.S. patent application Ser. No. 11/429,377, filed May 4, 2006, entitled "Flexible Tissue Rasp," and also claims the benefit under 35 USC 119(e) of U.S. Provisional Patent Application No. 60/869,070, filed Dec. 7, 2006, entitled "Flexible Tissue Removal Devices and Methods," both of which are hereby incorporated fully by reference. The present application is related to, but does not claim priority from, PCT Patent Application Pub. No. PCT/US2005/037136, titled "Devices and Methods for Selective Surgical Removal of Tissue, filed Oct. 15, 2005, which is hereby incorporated fully by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates generally to medical/surgical devices and methods. More specifically, the present invention relates to flexible tissue modification devices and methods.

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. It may also be advantageous to have minimally invasive or less invasive tissue modification devices capable of treating target tissues in parts of the body other than the spine. At least some of these objectives will be met by the present invention.

BRIEF SUMMARY OF THE INVENTION

In various embodiments, devices, systems and methods of the present invention provide for minimally invasive or less invasive modification of tissue in a patient. For the purposes of this application, the phrase "tissue modification" includes any type of tissue modification, such as but not limited to removing, cutting, shaving, abrading, shrinking, ablating, shredding, sanding, filing, contouring, carving, melting, heating, cooling, desiccating, expanding, moving, delivering medication or other substance(s) to tissue and/or delivering an implantable device, such as a stent, to tissue to modify the tissue's configuration, shape, position or the like.

In one aspect of the present invention, a device for modifying tissue in a patient may include: an elongate body having a rigid proximal portion and a flexible distal portion having first and second major surfaces; a proximal handle coupled with the proximal portion of the body; one or more tissue modifying members disposed along the first major surface of the distal portion of the body; a guidewire coupled with and extending from the distal portion of the body; and a distal handle removably couplable with the guidewire outside the patient. In some embodiments, the device may be configured to modify spinal tissue, and the device may be configured to extend into the patient's body, along a curved path through an intervertebral foramen of the spine, and out of the patient's body, such that at least part of the flexible distal portion of the elongate body of the device extends into the intervertebral foramen, and the proximal and distal handles reside outside the patient. In one embodiment, a height of the tissue modifying member(s) may be greater than a thickness of a ligamentum flavum of the spine. In alternative embodiments, the device may be configured for use in modifying any of a number of other tissues in the spine or in other parts of a patient's body. In one embodiment, for example, a device may be used to incise the transverse carpal ligament while inhibiting damage of the median nerve to perform a minimally invasive carpal tunnel release procedure. Other tissues in the knee, shoulder, elbow, foot, ankle or other parts of the body may be addressed in alternative embodiments.

In various alternative embodiments, the tissue modifying member(s) of a tissue modification device may include, but are not limited to, one or more uni-directional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials and/or deliverable substances adhered to or formed in the first major surface. Some embodiments may include one type of tissue modifying member, while other embodiments may include a combination of different tissue modifying members. In some embodiments, the tissue modifying member(s) may be fixedly attached to or formed in the first major surface, and the device may operate by reciprocating the entire device (or most of it) back and forth to cause the tissue modifying member(s) to modify tissue. In alternative embodiments, the tissue modifying member(s) may be moveably attached to or formed in the first major surface, and the device may further include an actuator coupled with the tissue modifying member(s) and extending to the proximal handle for actuating the tissue modifying member(s).

In one embodiment, the elongate body may be at least partially hollow, the distal portion may be flatter than the proximal portion, and the tissue modifying members may comprise blades formed in the first major surface of the distal portion. In some embodiments, the guidewire may be removably coupled with the distal portion of the elongate body via a guidewire coupler comprising a cavity for containing a shaped tip of the guidewire, and wherein the guidewire comprises at least one shaped tip for fitting within the cavity.

Some embodiments may further include a material disposed over a portion of the elongate body distal portion to provide the distal portion with smooth edges. For example, such a material may comprise, in some embodiments, a polymeric cover disposed over the distal portion with one or more openings through which the tissue modifying member(s) protrude. In one embodiment, the material may be further configured to collect tissue removed by the tissue modifying member(s). In some embodiments, the device may include a tissue collection chamber formed in or attached to the elongate body.

In another aspect of the present invention, a device for modifying tissue in a patient may include an elongate body, a proximal handle coupled with the proximal portion of the body, one or more tissue modifying members disposed along the first major surface of the intermediate portion of the body, and a distal handle removably couplable with the distal portion of the body outside the patient. In some embodiments, the elongate body may include a rigid proximal portion, a flexible distal portion, and an intermediate flexible portion disposed between the proximal and distal portions and having first and second major surfaces. In some embodiments, the device may be configured to modify spinal tissue, and the device may be configured to extend into the patient's body, along a curved path through an intervertebral foramen of the spine, and out of the patient's body, such that at least part of the flexible intermediate portion of the elongate body of the device extends into the intervertebral foramen, and the proximal and distal handles reside outside the patient.

In some embodiments, the distal portion of the elongate body may comprise a guidewire coupled with the intermediate portion of the body. In some embodiments, at least the proximal and intermediate portions of the elongate body are at least partially hollow, thus forming at least one lumen. For example, in some embodiments, the at least one lumen may include a suction lumen and/or an irrigation lumen. Optionally, some embodiments may include at least one tissue transport member slidably disposed within the lumen and configured to remove tissue out of the device. For example, in one embodiment the tissue transport member may comprise one or more flexible wires having tissue collection portions disposed under the tissue modifying member(s) of the device. Such tissue collection portions may include, for example, shaped portions of the wire(s), adhesive coating(s) on the wire(s), tissue collecting material(s) on the wire(s), adhesive material(s) used to make the wire(s) themselves and/or the like. In alternative embodiments, the tissue transport member may comprise a piece of tissue adhering material disposed under the tissue modifying member(s) of the device. In other alternative embodiments, the tissue transport member may comprise a removable tissue collection chamber disposed under the tissue modifying member(s) of the device. Alternatively, the tissue transport member may comprise at least one unidirectional valve for allowing tissue to pass through the shaft toward the proximal handle while preventing the cut tissue from passing through the valve(s) toward the tissue modifying member(s) of the device.

In some embodiments, at least part of the elongate body may be sufficiently flexible to be compressible, such that tissue may be moved through the elongate body by compressing the compressible portion. Some embodiments of the device may further include a tissue collection chamber formed in or attached to the elongate body.

In another aspect of the present invention, a kit for modifying tissue in a patient may include a tissue modification device, a guidewire configured to couple with a guidewire coupler of the device, and a distal handle removably couplable with the guidewire outside the patient. The tissue modification device may include a rigid shaft having a proximal end and a distal end, a flexible substrate extending from the distal end of the shaft, a proximal handle coupled with the shaft at or near its proximal end, one or more tissue modifying members disposed along one side of the substrate, and a guidewire coupler disposed on the substrate. In some embodiments, the tissue modification device and guidewire, coupled together, may be configured to extend into the patient's body, along a curved path through an intervertebral foramen of the spine, and out of the patient's body, such that at least part of the flexible substrate extends into the intervertebral foramen, and the proximal and distal handles reside outside the patient.

Optionally, some embodiments may also include at least one probe for passing the guidewire between target and non-target tissues in a patient. For example, in some embodiments, the probe may comprise a needle. In alternative embodiments, the probe may comprise a curved, cannulated probe. In any case, a probe may optionally include a flexible guide member for passing through the probe, and such a guide member may have an inner diameter selected to allow passage of the guidewire therethrough.

In some embodiments, the tissue modification device may further include a tissue collection member coupled with the substrate and configured to collect tissue. Such an embodiment may optionally further include tissue transport means configured to transport the collected tissue through the device.

In another aspect of the present invention, a method for modifying target tissue in a patient while inhibiting damage to non-target tissues may involve: advancing a flexible distal portion of an elongate tissue modification device into the patient's body and along a curved path between target and non-target tissues, such that a distal end of the distal portion exits the patient's body; coupling a first handle with the distal portion outside the patient; applying a first tensioning force to the first handle; applying a second tensioning force to a second handle coupled with a rigid proximal portion of the device, the first and second tensioning forces urging one or more tissue modifying members disposed along the flexible distal portion against the target tissue; and reciprocating at least a portion of the device back and forth, while maintaining at least some of the tensioning force, to cause the tissue modifying member(s) to modify the target tissue.

In some embodiments, advancing the distal portion may involve advancing through an intervertebral foramen of the patient's spine, and reciprocating the device may involve modifying ligamentum flavum and/or bone. In some embodiments, advancing the distal portion may involve advancing percutaneously into the patient. In some embodiments, the distal portion of the device may be advanced into the patient's spine without removing bone, and only ligamentum flavum tissue may be modified. The method may optionally further involve manipulating the second handle and thus the rigid proximal portion to steer the flexible portion of the device.

In one embodiment, the flexible distal portion may include a flexible substrate coupled with a flexible guidewire, coupling the first handle may involve coupling with the guidewire, and advancing the distal portion may involve pulling the guidewire with the first handle to advance the flexible substrate between the target and non-target tissue. In various embodiment, the target tissue may include, but is not limited to, ligament, tendon, bone, tumor, cyst, cartilage, scar, osteophyte and inflammatory tissue, and the non-target tissue may include, but is not limited to, neural tissue and neurovascular tissue. In one embodiment, for example, the target tissue may include a transverse carpal ligament, and the non-target tissue may include a median nerve.

In some embodiments, the tensioning forces may urge a plurality of tissue modifying members against a curved target tissue along a length of the flexible portion. In some embodiments, reciprocating at least a portion of the device may involve reciprocating an entire portion between the first and second handles, and reciprocating may cause a tissue modifying surface of the flexible portion to modify the target tissue while an atraumatic surface of the flexible portion faces the non-target tissue. In alternative embodiments, reciprocating at least a portion of the device may involve reciprocating a tissue modifying surface of the flexible portion, and reciprocating may cause the tissue modifying surface to modify the target tissue while an atraumatic surface of the flexible portion faces the non-target tissue.

Optionally, in some embodiments, the method may further involve collecting cut tissue in the tissue modification device. In some embodiments, the method may additionally include transporting the cut tissue out of the patient through the tissue modification device. For example, transporting the cut tissue may involve applying suction and/or irrigation in the tissue collection chamber. Alternatively, transporting the cut tissue may involve collecting the cut tissue on or in one or more tissue transport members and withdrawing the tissue transport member(s) through the tissue modification device.

In another aspect, the invention provides a method for removing a target ligament and/or bone tissue of a patient. The method comprises providing an elongate body having an axis and an elongate, axially flexible portion affixed to a rigid shaft portion. The flexible portion is positioned within the patient so that a first surface of the flexible portion is oriented toward the target tissue. The first surface is shifted toward a target region of the target tissue by moving the rigid portion, and the target region of the target tissue is removed with a tissue modifying member disposed along the first surface.

Optionally the rigid portion extends axially from a first end of the flexible portion. The flexible portion can be flexible in one lateral orientation, and may be stiffer in another lateral orientation (for example, in the direction in which it is shifted). The flexible portion can be positioned so that the first surface of the flexible portion bends over the target tissue, and/or the flexible portion may be axially tensioned to urge the first surface toward the target tissue. The tension can be applied to the first end by pulling the rigid portion from outside the patient.

In many embodiments, the surface will be shifted by applying torque to the rigid portion from outside the body portion. The rigid portion can then rotate the flexible portion about the axis so as to shift an orientation of the first surface toward a target region of the target tissue. Where the target tissue has a convex surface defining an outward orientation and an inward orientation, and where the first surface is bordered by first and second opposed edges, the target tissue adjacent the first edge may be inward of the target tissue adjacent the second edge. As a result, the tension of the flexible portion may induce rolling of the flexible portion about the axis toward the first edge. The torquing of the shaft portion may counteract the tension-induced rolling to inhibit flipping of the flexible portion.

A distal handle may be coupled with a second end of the flexible portion, and the flexible portion may be manually tensioned by simultaneous pulling, from outside the patient, on the first and second handles. Axially moving the tissue modifying member along a curving path may be performed within the patient by relative movement between the first and second handles, the curving path including the bend over the target tissue. Lateral translation of the rigid portion from outside the patient can be used to induce the lateral shifting of the first surface, particularly where the flexible portion is stiffer in a second lateral orientation extending along the first surface, with the first surface typically shifting along that second lateral orientation.

In some embodiments, pivoting of the rigid portion about tissues disposed along the rigid portion may be used to induce the lateral shifting of the first surface. Optionally, a first handle may be attached to the rigid portion outside the patient, and the flexible portion can be manually tensioned and shifted by manipulating the first handle with a hand. A distal handle can be coupled with a second end of the flexible portion, and the flexible portion can be manually tensioned by simultaneous pulling, from outside the patient, on the first and second handles. Axially moving of the tissue modifying member along a curving path within the patient can be effected by relative movement between the first and second handles, typically with the curving path including a bend over the target tissue. Reciprocation of the tissue modifying member along the curved path and against the target tissue can be provided by sequentially pulling on the first and second handles so that a cutting edge of the tissue modifying member incises the target tissue. In some embodiments, another rigid portion extends from the second handle to the second end of the flexible portion inside the patient, with the first surface of the flexible portion being shifted using both rigid portions.

In yet another aspect, the invention provides a system for removing a target tissue of a patient. The system comprises an elongate flexible portion having a first end and a second end with an axis therebetween. The flexible portion has a first surface extending along the axis and is axially bendable in a first lateral orientation. A rigid portion is extendable from the flexible body portion so that pulling on the rigid portion can axially tension the flexible portion to urge the first surface toward the target tissue. Movement of the rigid portion can be used to shift the first surface toward a target region of the target tissue. A tissue modifying member disposed along the first surface can be configured to effect removal of the target region of the target tissue.

These and other aspects and embodiments are described more fully below in the Detailed Description, with reference to the attached Drawings.

DETAILED DESCRIPTION OF THE INVENTION

Various embodiments of tissue modification devices and systems, as well as methods for making and using same, are provided. Although much of the following description and accompanying drawing figures generally focuses on surgical procedures in spine, in alternative embodiments, devices, systems and methods of the present invention may be used in any of a number of other anatomical locations in a patient's body. For example, in some embodiments, flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, any of a number of other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions.

Figure 1:
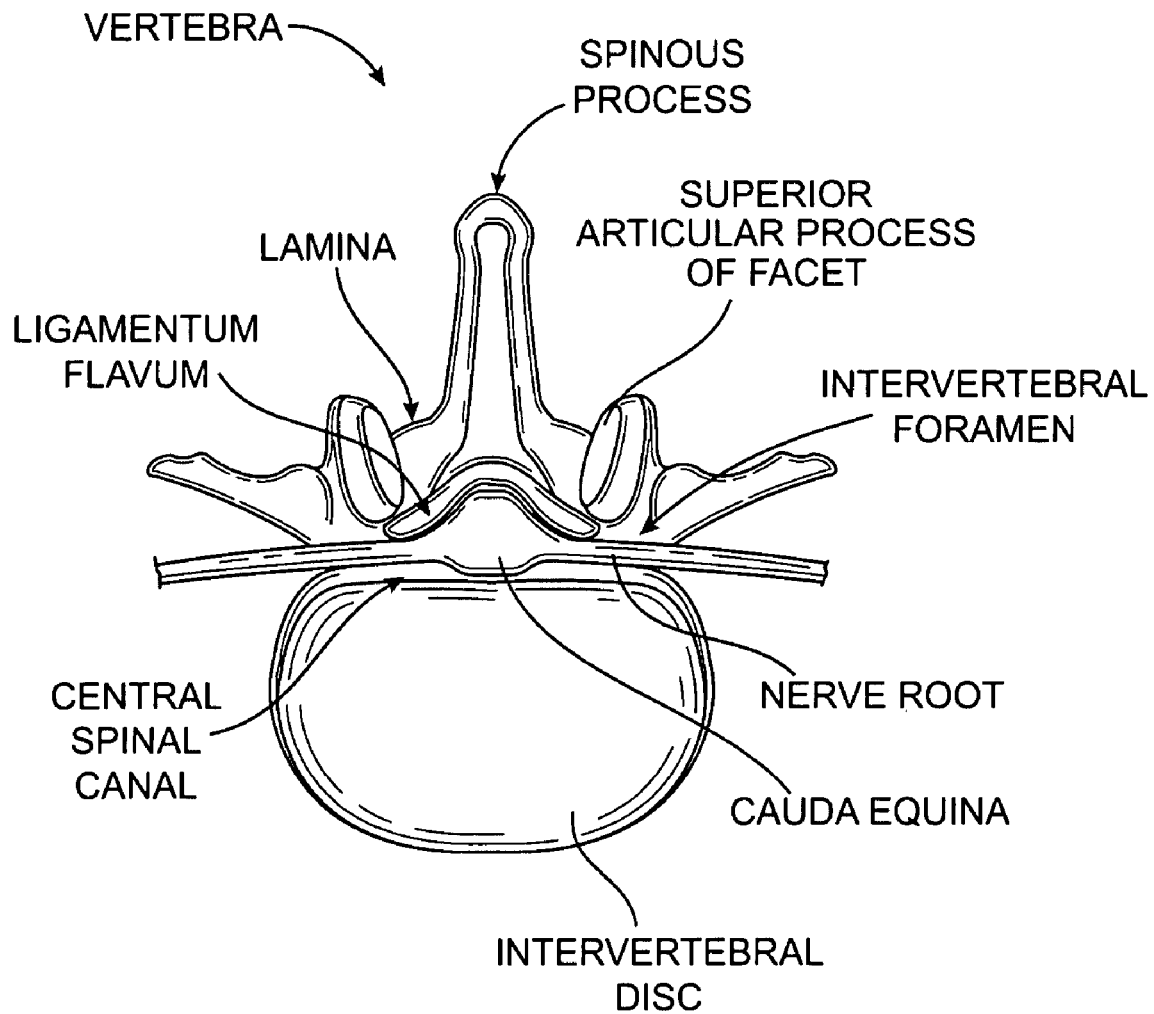
FIG. 1 is a top view of a vertebra with the cauda equina shown in cross section and two nerve roots branching from the cauda equina to exit the central spinal canal and extend through intervertebral foramina on either side of the vertebra.
Figure 2A:
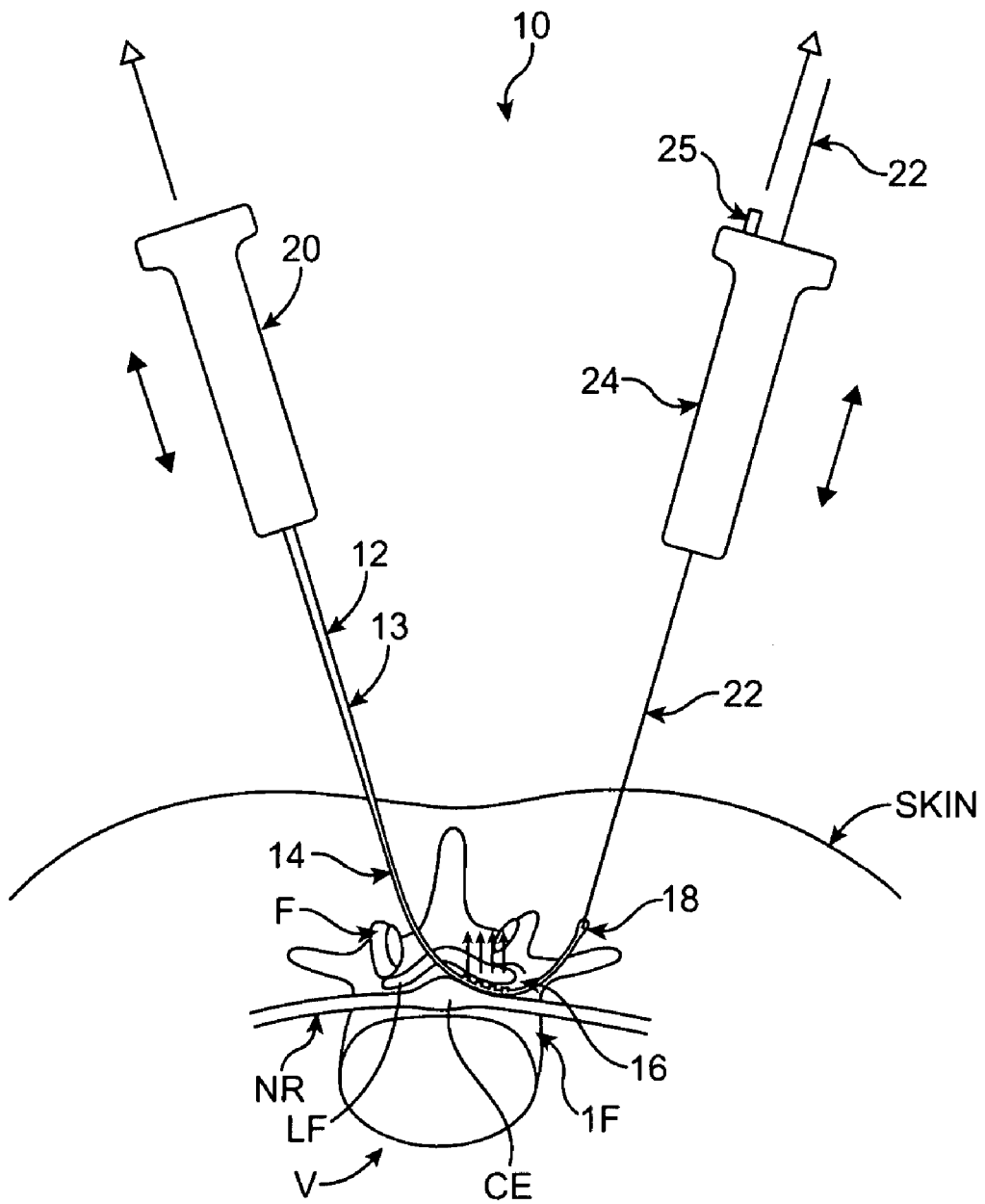
FIG. 2A is a cross-sectional view of a patient's back and a side view of a flexible tissue modification device in position in a spine, according to one embodiment of the present invention.

With reference now to FIG. 2A, a tissue modification device 10 according to one embodiment may suitably include a proximal handle 20 coupled with a shaft 12 having a proximal, rigid portion 13 and a distal, flexible portion 14 on which one or more tissue modifying members 16 may be disposed. A guidewire coupler 18 may be formed in (or attached to) flexible portion 14 at or near its distal end, for coupling with a guidewire 22, which in turn may be coupled with a guidewire handle 24 (or "distal handle"), which may include a tightening lever 25 for tightening handle 24 around guidewire 22.

Device 10 is shown percutaneously placed in position for performing a tissue modification procedure in a patient's spine, with various anatomical structures shown including a vertebra V, cauda equina CE, ligamentum flavum LF, nerve root NR, facet F, and intervertebral foramen IF. Various embodiments of device 10 may be used in the spine to remove ligamentum flavum LF, facet bone F, bony growths, or some combination thereof, to help decompress cauda equina CE and/or nerve root NR tissue and thus help treat spinal stenosis and/or neural or neurovascular impingement. Although this use of device 10 will not be continuously repeated for every embodiment below, any of the described embodiments may be used to remove ligamentum flavum alone, bone alone, or a combination of ligament and bone in the spine to treat neural impingement, neurovascular impingement and/or spinal stenosis.

In one embodiment of a method for modifying tissue using device 10, a distal end of 22 guidewire may be placed into the patient, along a curved path between target and non-target tissue, and out of the patient. A distal portion of guidewire 22 may then be coupled with guidewire handle 24, such as by passing guidewire 22 through a central bore in handle 24 and tightening handle 24 around guidewire 22 via tightening lever 25 or other tightening means. A proximal end of guidewire 22 may then be coupled with coupling member 18 and used to pull distal shaft portion 14 between target and non-target tissues. In some embodiments, device 10 may be advanced into the patient percutaneously, while in alternative embodiments, device 10 may be advanced through a small incision or larger incision. Once advanced into the patient, flexible distal shaft portion 14 may be advanced along a curved path between the target and non-target tissues, and in some instances may be pulled at least partway into an intervertebral foramen IF of the spine.

Proximal handle 20 and guidewire handle 24 may be pulled (or "tensioned"—solid/single-tipped arrows) to urge tissue modifying members 16 against the target tissue (in this case, ligamentum flavum LF). Generally, tissue modifying members 16 may be fixedly attached to (or formed in) on one side or surface of distal portion 14, while an opposite side or portion of distal portion 14 faces non-target tissue, such as cauda equina CE and/or nerve root NR. The opposite side of distal portion 14 will generally be atraumatic and/or include an atraumatic cover, coating, shield, barrier, tissue capture member or the like. With tensioning force applied to device 10, handles 20, 24 may be used to reciprocate device 10 back and forth (solid/double-tipped arrows) to cause tissue modifying members 16 to cut, remove, shred or otherwise modify the target tissue. In various embodiments, for example, target tissue may include only ligamentum flavum LF, only bone, or a combination of both.

Reciprocation and tensioning may be continued until a desired amount of tissue is removed. Removed target tissue, in some embodiments, may be collected, captured or trapped between tissue modifying members 16 and/or in one or more tissue capture members or chambers (not shown). When a desired amount of target tissue has been removed, which may be determined, for example, by tactile feedback provided to the surgeon by device 10, by radiographic imaging, and/or by direct visualization (such as in an open surgical case), guidewire 22 may be released from distal handle 24, and device 10 may be removed from the patient's back. If desired, device 10 may be passed into the patient's spine again for additional tissue modification, and/or other devices may be passed into the spine.

Additional details of various methods for inserting and using device 10 are provided below. For further explanation of guidewire systems and methods for inserting devices to remove or otherwise modify tissue, reference may also be made to U.S. patent application Ser. Nos. 11/468,247 and 11/468,252, both titled "Tissue Access Guidewire System and Method," and both filed Aug. 29, 2006, the full disclosures of which are hereby incorporated by reference.

Figure 2B:
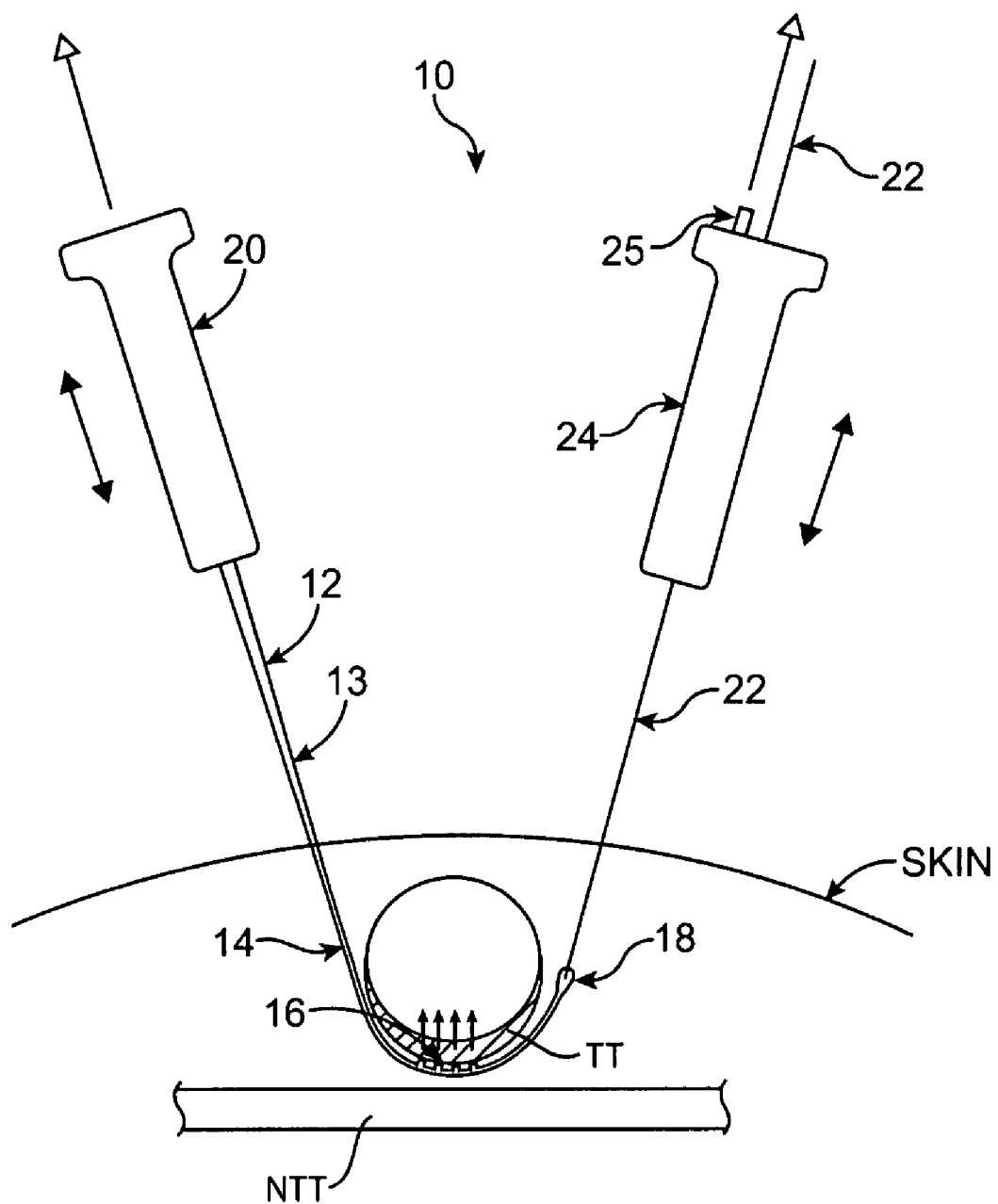
FIG. 2B is a diagrammatic view of a generic portion of a patient's body, showing target and non-target tissue, with the device of FIG. 2A in position to modify target tissue, according to one embodiment of the present invention.

Referring now to FIG. 2B, in various embodiments, device 10 may be used in parts of the body other than spine to remove target tissue TT while avoiding harm to non-target tissue NTT. For example, target tissue TT may include soft tissue adhering to bone, such as ligament and/or cartilage, and/or may include bone. Non-target tissue NTT may include any nervous tissue, vascular tissue, an organ, or any other tissue that a surgeon may desire to leave unharmed by a surgical procedure. In one embodiment, for example, device 10 may be used to perform a minimally invasive carpal tunnel release procedure by releasing the transverse carpal ligament without damaging the median nerve. In some embodiments, such a procedure may be performed percutaneously with or without an endoscope. In other embodiments, device 10 may be used to remove cartilage and/or ligament from a knee or shoulder in a minimally invasive procedure. In yet another embodiment, device 10 may be used to perform a minimally invasive bunionectomy. Therefore, although the following discussion focuses primarily on various uses of alternative embodiments of device 10 in spine, any of a number of other anatomical structures may be operated upon in different embodiments.

Figure 2C:
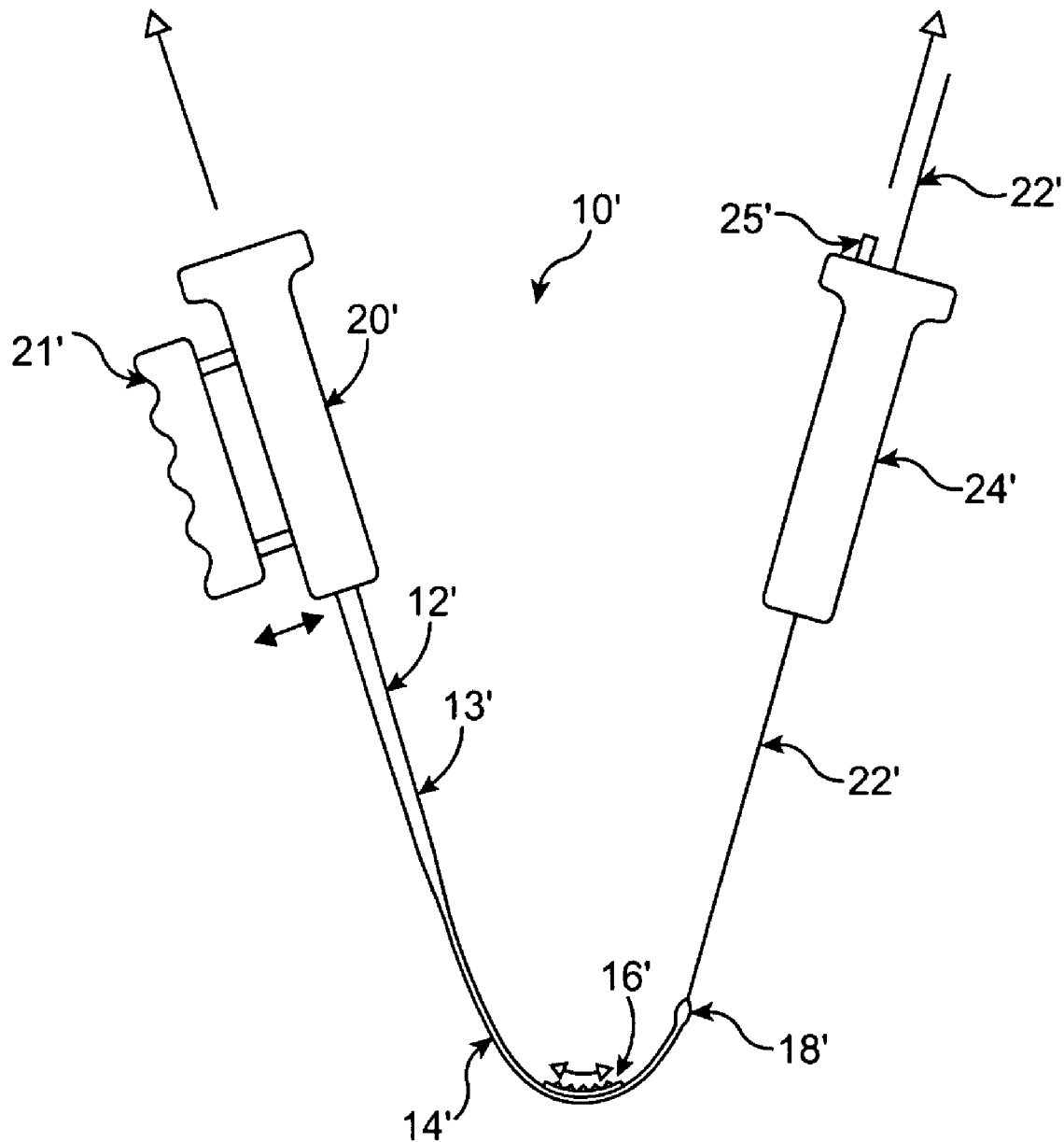
FIG. 2C is a side view of a tissue modification device, according to an alternative embodiment of the present invention.

Referring now to FIG. 2C, in an alternative embodiment, a tissue modification device 10' may suitably include a proximal handle 20', including a squeeze actuator 21' and coupled with a shaft 12' having a proximal, rigid portion 13' and a distal, flexible portion 14'. One or more tissue modifying members 16' may be moveably coupled with one side of flexible portion 14', and a guidewire coupler 18' may be formed in (or attached to) flexible portion 14' at or near its distal end, for coupling with a guidewire 22' and thus a distal handle 24' with a tightening lever 25'.

In this alternative embodiment, squeeze actuator 21' may be coupled with moveable tissue modifying members 16' by any suitable means, such that actuating actuator 21' (double-headed, solid-tipped arrow) causes tissue modifying members 16' to reciprocate back and forth (double-headed, hollow-tipped arrow). In use, therefore, device 10' as a whole may be held relatively stationary, while tissue modifying members 16' are reciprocated. Proximal handle 20' and rigid proximal shaft portion 13' may be used to steer device 10' relative to target tissue, and of course device 10' may be moved in and out of the patient and/or the target tissue, but it may also be possible to hold device 10' relatively stationary while reciprocating tissue modifying members 16'. In various embodiments, squeeze actuator 21' may be replaced with any suitable mechanical actuator, such as a trigger, lever or the like.

Figure 2D:
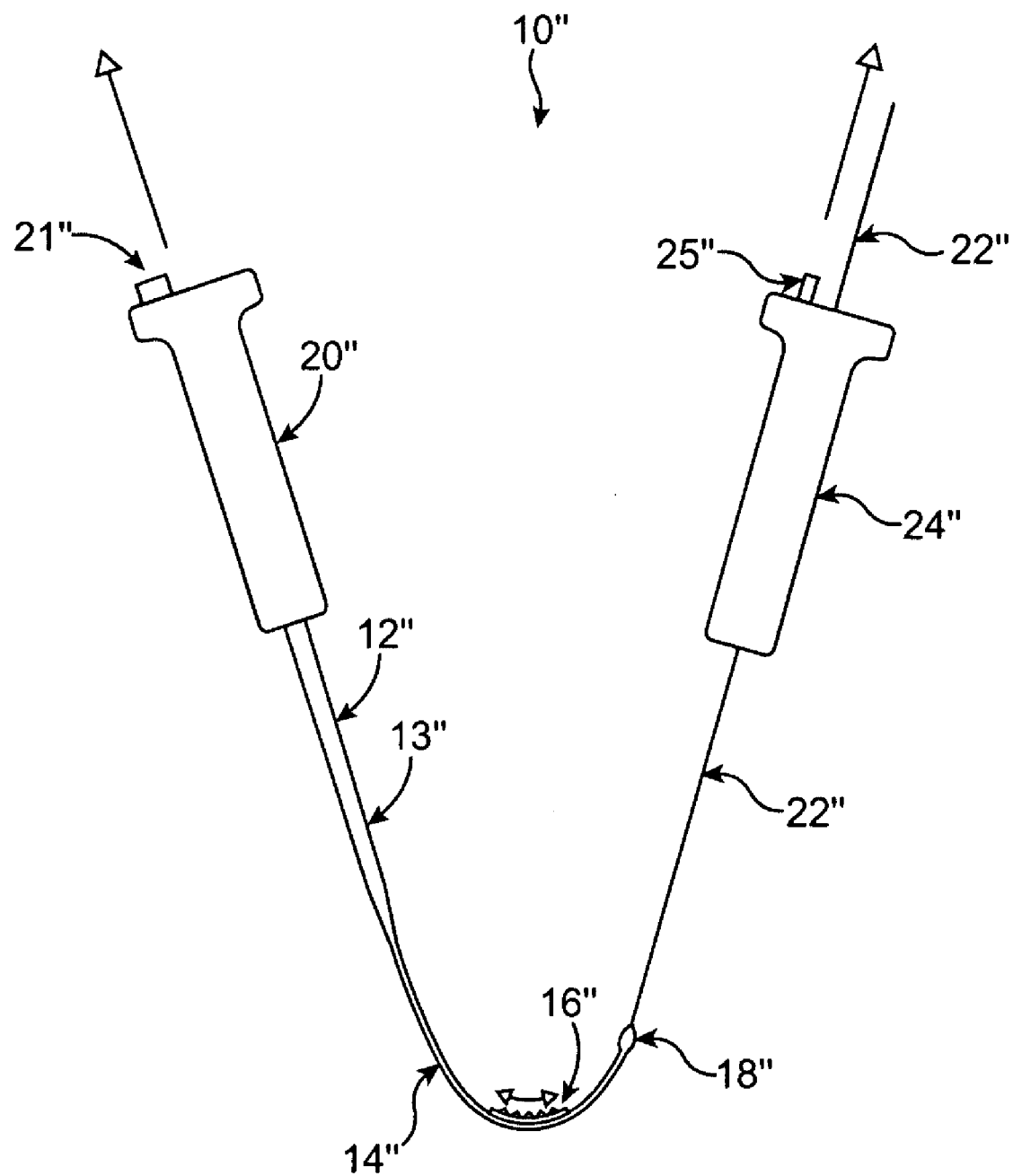
FIG. 2D is a side view of a tissue modification device, according to another alternative embodiment of the present invention.

With reference now to FIG. 2D, in another alternative embodiment, a tissue modification device 10" may be similar to the previous embodiment but may include, instead of squeeze actuator 21', a button actuator 21" and a powered drive mechanism within handle 20'". Pressing button actuator 21" may activate tissue modifying members 16" to reciprocate back and forth to modify tissue. In various alternative embodiments, button 21" may be replaced with any suitable actuator, such as a trigger, switch, dial or the like.

Figure 3A:
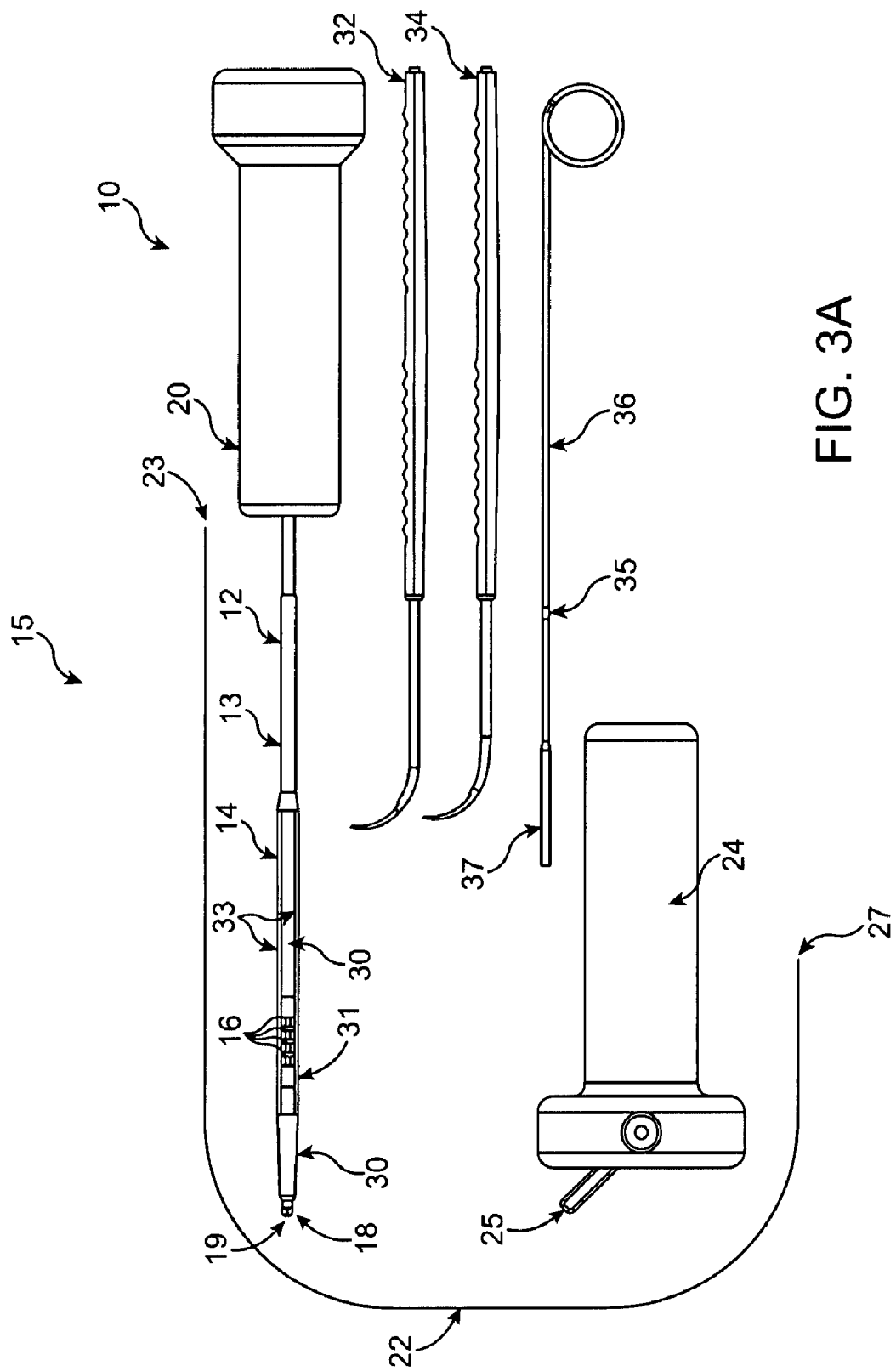
FIG. 3A is a view of a kit or system for modifying tissue, according to one embodiment of the present invention.

With reference now to FIG. 3A, in some embodiments tissue modification device 10 may be provided as a system (or "kit"), including the various components described above in reference to FIGS. 2A and 2B. In some embodiments, a tissue modification system 15 or kit may suitably include device 10 of FIGS. 2A and 2B, as well as one or more additional devices or components. For example, multiple guidewires 22 may be provided as part of system 15. In some embodiments, system 15 may also include one or more guidewire passage probes 32, 34 and a curved, flexible guide member 36. In one embodiment, for example, an ipsilateral access probe 32 and a contralateral access probe 34 may be provided. Curved guide member 36 is generally configured to pass through a lumen in each of probes 32, 34 and includes an inner lumen through which guidewire 22 may be passed. Guide member 36 may further include one or more depth marks 35 to indicate to a surgeon when guide member 36 has been passed a certain distance into probe 32, 34 and a stop 37 to limit passage of guide member 36 farther into probe 32, 34. In an alternative embodiment (not shown), such as might be used in a completely percutaneous procedure, probes 32, 34 may be replaced with an introducer needle, such as but not limited to a 14 gauge Touhy epidural needle or other size or type of epidural needle. In such an embodiment, guide member 36 may be designed to pass through the bore of the needle. For further description of various probe and guide member devices, reference may be made to U.S. patent application Ser. Nos. 11/468,247 and 11/468,252. Further reference may be made to U.S. patent application Ser. No. 11/457,416, titled "Spinal Access and Neural Localization," and filed Jul. 13, 2006; and 60/823,594, titled "Surgical Probe and Method of Making," and filed Aug. 25, 2006, the full disclosures of which are hereby incorporated by reference.

Guidewire 22 may be made of any suitable material, such as nitinol or stainless steel, and may include a sharp distal tip 23, to facilitate passage of guidewire 22 through tissue, and a proximal shaped end 27 for coupling with guidewire coupler 18. Further details of various guidewire 22 embodiments and distal handle 24 are provided, for example, in U.S. patent application Ser. Nos. 11/468,247 and 11/468,252, which were previously incorporated by reference.

Figure 3B:
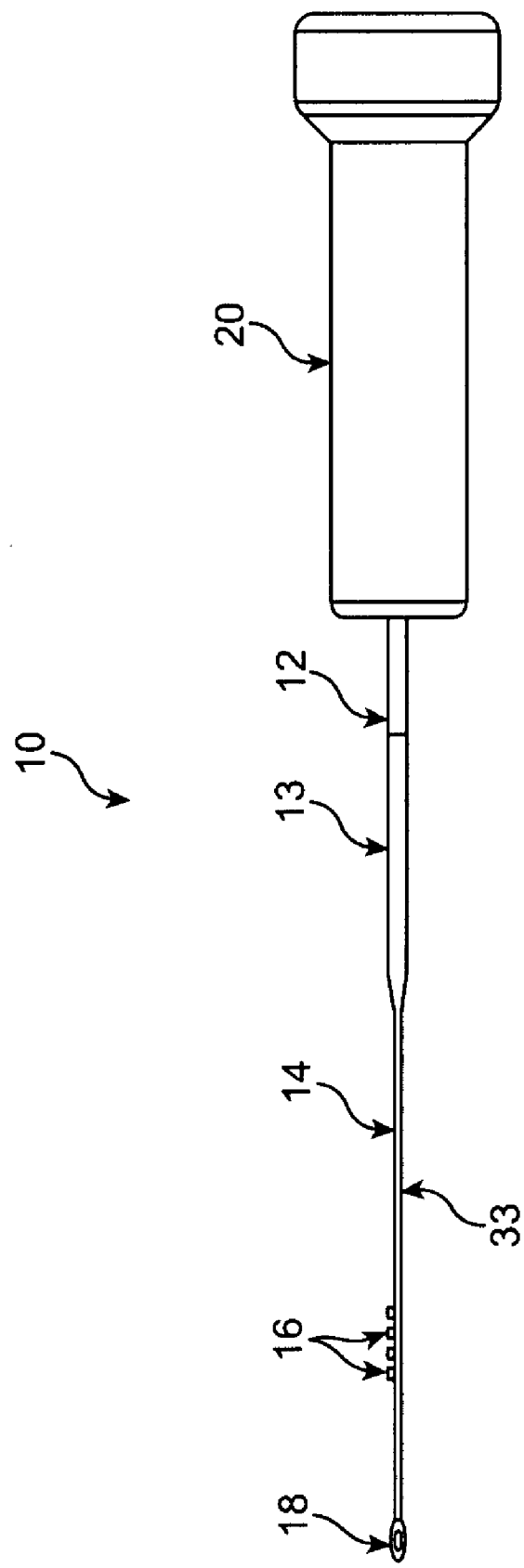
FIG. 3B is a side view of a portion of the kit of FIG. 3A.

FIGS. 3A and 3B show proximal handle 20 and shaft 12 in greater detail than in previous figures. In the embodiment shown, four tissue modifying members 16 are fixedly attached to one side of flexible distal shaft portion 14, each comprising grooved blades with bi-directional cutting edges. In various alternative embodiments, any number of tissue modifying members 16 may be included, such as from one to twenty tissue modifying members 16. Furthermore, tissue modifying members 16 may have any of a number of different configurations, some of which are described below, such unidirectional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials, deliverable substances and/or the like.

In various embodiments, proximal shaft portion 13, distal shaft portion 14, tissue modifying members 16 and guidewire coupler 18 may be made of any suitable material (or materials), and may be made from one piece of material as a single extrusion or from separate pieces attached together. For example, in many embodiments, all of shaft 12 and guidewire coupler 18 may be made from one piece of material, and tissue modifying members 16 may be attached to distal shaft portion 14, such as by welding. In alternative embodiments, however, guidewire coupler 18 may be a separate piece attached to distal shaft portion 14 and/or tissue modifying members 16 may be formed in (rather than attached to) distal shaft portion 14. In yet another embodiment, distal shaft portion 14 may comprise a flat piece of material coupled with rigid proximal shaft portion 13, such as by welding. In some embodiments, shaft 12 may be formed from one piece of material, and distal shaft portion 14 may be flattened to derive its shape and flexibility. In some embodiments, one or more slits may be formed in distal shaft portion 14, to enhance its flexibility. In some embodiments, proximal shaft portion 13 may have a cylindrical shape. In some embodiments proximal shaft portion 13, distal shaft portion 14, or both may be hollow. Alternatively, any portion of shaft 12 may be solid in some embodiments, such as to give proximal shaft portion 13 added rigidity.

In one embodiment, guidewire coupler 18 may include a slot 19, shaped to receive and hold guidewire proximal shaped end 27. In various embodiments, slot 19 may be located on the top surface of distal shaft portion 14, as shown, or on the bottom surface. For further description of various embodiments of guidewire couplers, reference may be made to U.S. patent application Ser. Nos. 11/468,247 and 11/468, 252. In some embodiments, an atraumatic cover 30 may be disposed over part of distal shaft portion 14, forming atraumatic edges 33 and an aperture 31 through which tissue modifying members 16 protrude. Cover 30 may be made of any suitable atraumatic material, such as any of a number of different polymers. In some embodiments, cover 30 may also serve to collect cut tissue.

FIG. 3B is a side view of device 10. Tissue modifying members 16 may be seen extending above atraumatic edges 33 of cover 30 and having cutting edges facing both proximally and distally. In alternative embodiments, tissue modifying members 16 may have only uni-directional cutting edges, such as facing only proximally or only distally. In the embodiment shown, guidewire coupler 18 is formed as a loop at the distal end of distal shaft portion 14. Guidewire shaped end 27 may generally fit into slot 19 (not visible in FIG. 3B) to reside within the loop of guidewire coupler 18 during use. In other embodiments, guidewire coupler 18 may comprise a separate piece attached to the top side or bottom side of distal shaft portion 14. Examples of such embodiments are described further in U.S. patent application Ser. Nos. 11/468, 247 and 11/468,252.

The various components of device 10, including proximal handle 20, shaft 12, tissue modifying members 16, guidewire coupler 18, and cover 30, may be fabricated from any suitable material or combination of materials. Suitable materials include, for example, metals, polymers, ceramics, or composites thereof. Suitable metals may include, but are not limited to, stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include, but are not limited to, nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include, but are not limited to, aluminas, zirconias, and carbides. In some embodiments, one or more portions of shaft 12, for example, may be reinforced with carbon fiber, fiberglass or the like.

Referring now to FIGS. 4A-4E, one embodiment of a method for modifying tissue using flexible tissue modification device 10 is demonstrated in greater detail. In these figures, a patient's skin, target tissue TT and non-target tissue NTT are shown diagrammatically, rather than as specific structures. In one embodiment, the method of FIGS. 4A-4E may be employed in the spine, to remove ligamentum flavum, bone or both, with device 10 passing through an intervertebral foramen between two vertebrae, as shown in FIG. 2A. In other embodiments, other tissue in other areas of the body may be removed.

Figure 4A:
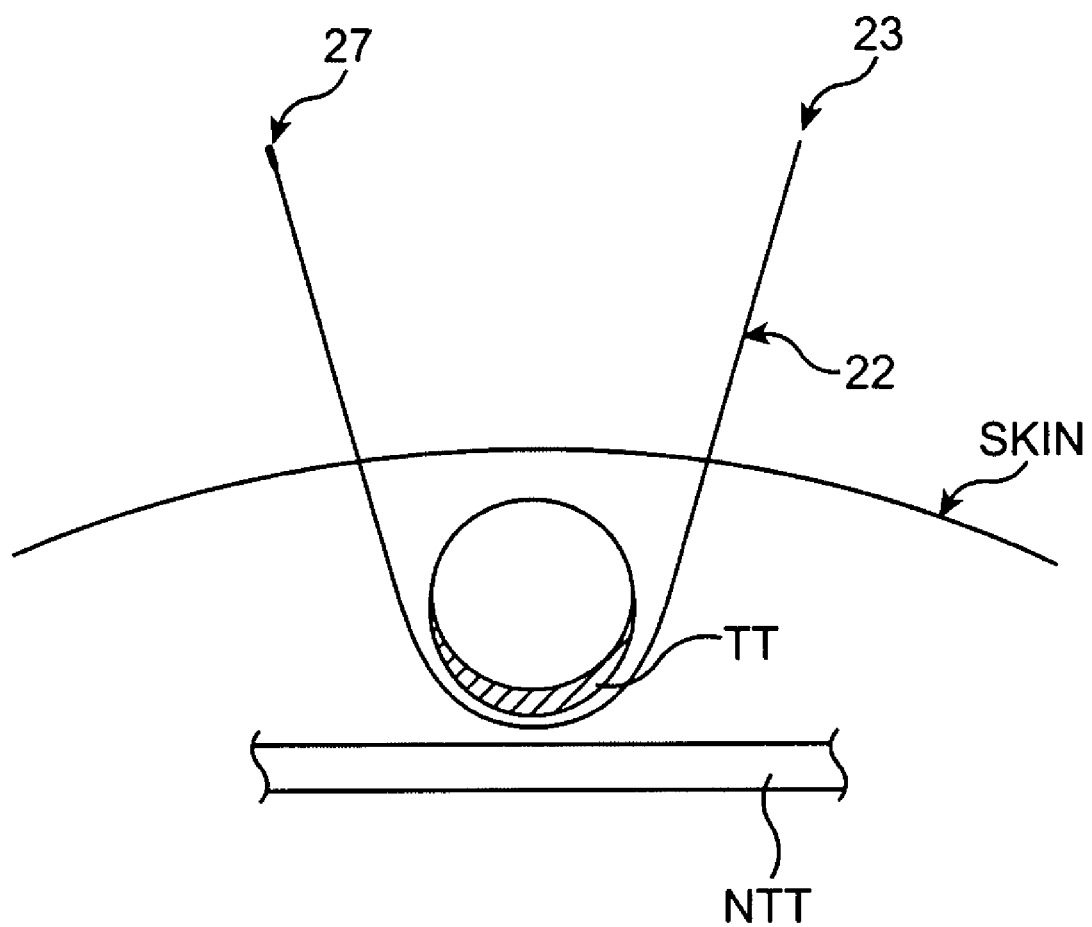
FIGS. 4A-4E demonstrate a method for inserting and using a flexible tissue modification device to modify tissue while inhibiting damage to non-target tissue, according to one embodiment of the present invention.

As shown in FIG. 4A, guidewire 22 with sharp tip 23 and shaped end 27 may be passed into the skin, between target and non-target tissue, and out of the skin. Methods for passing guidewire 22 are described further, for example, in U.S. patent application Ser. Nos. 11/457,416, 11/468,247 and 11/468,252, which were previously incorporated by reference. As described in those references, in various embodiments, guidewire 22 may be placed using a percutaneous method, such as with a needle, or using an open method, such as with a probe. In some embodiments, localization of neural tissue, such as with nerve stimulation on a guidewire passing probe or guidewire passing guide member may be used, to confirm that guidewire 22 is passed between target and non-target tissue.

In some embodiments where the method is performed in the spine, one or more substances or devices may be placed into the epidural space of the spine before or after placing guidewire 22, to create additional space between target tissues, such as ligamentum flavum, and non-target tissues, such as cauda equina and nerve root. Substances may include, for example, any of a number of fluids or gels, such as radiographic contrast medium. Devices may include, for example, a barrier or shield device. Injection of substances into the epidural space to create a safety zone is described in U.S. patent application Ser. No. 11/193,557 (Pub. No. 2006/0036211), titled "Spinal Ligament Modification Kit," assigned to X-Sten, Inc., and filed Jul. 29, 2005, the full disclosure of which is hereby incorporated by reference. Various barrier devices for placement in the spine are described, for example, in U.S. patent application Ser. No. 11/405,859, titled "Tissue Modification Barrier Devices and Methods," and filed Apr. 17, 2005, the full disclosure of which is hereby incorporated by reference.

Figure 4B:
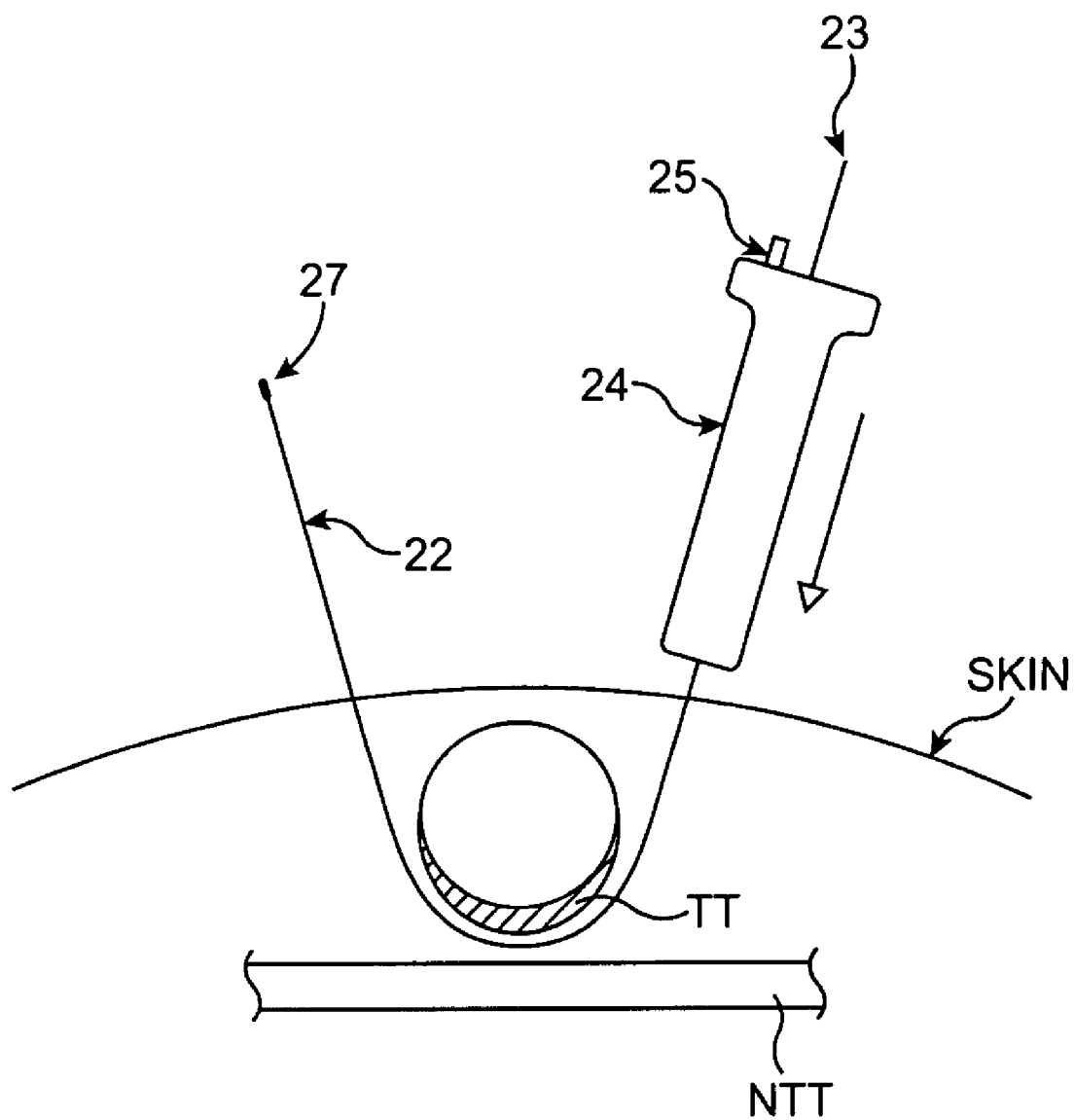

Referring to FIG. 4B, distal handle 24 may be passed over sharp tip 23 and tightened around guidewire 22, such as by moving tightening lever 25. Distal handle 24 may be coupled with guidewire 22 at this point in the process or at a later point, according to various embodiments.

Figure 4C:
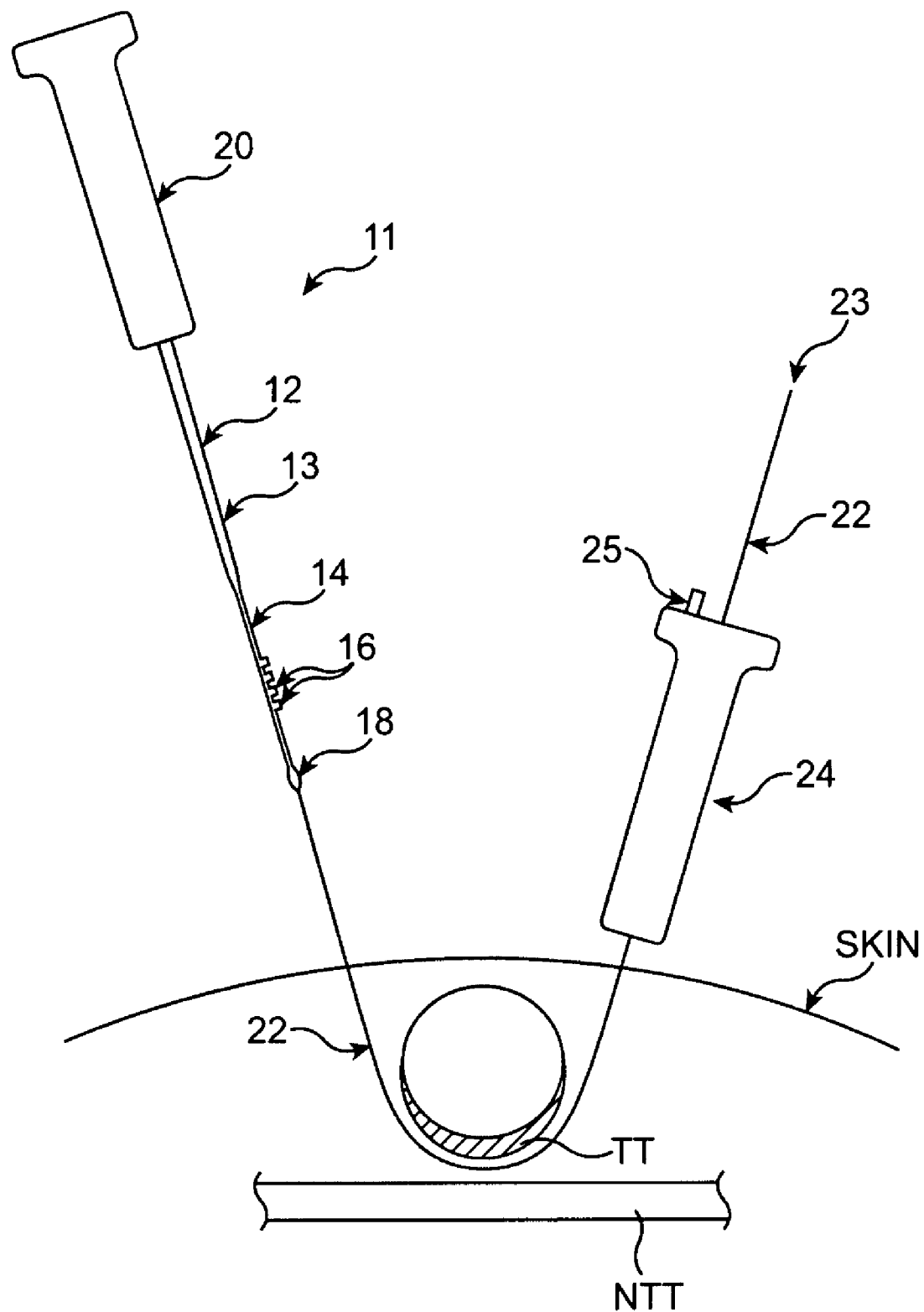

As shown in FIG. 4C, guidewire 22 may next be coupled with proximal device portion 11, by coupling shaped guidewire end 27 (not visible) with guidewire coupler 18. In the embodiment shown, for example, guidewire shaped end 27 may be placed into coupling member 18 (hollow-tipped arrow).

Figure 4D:
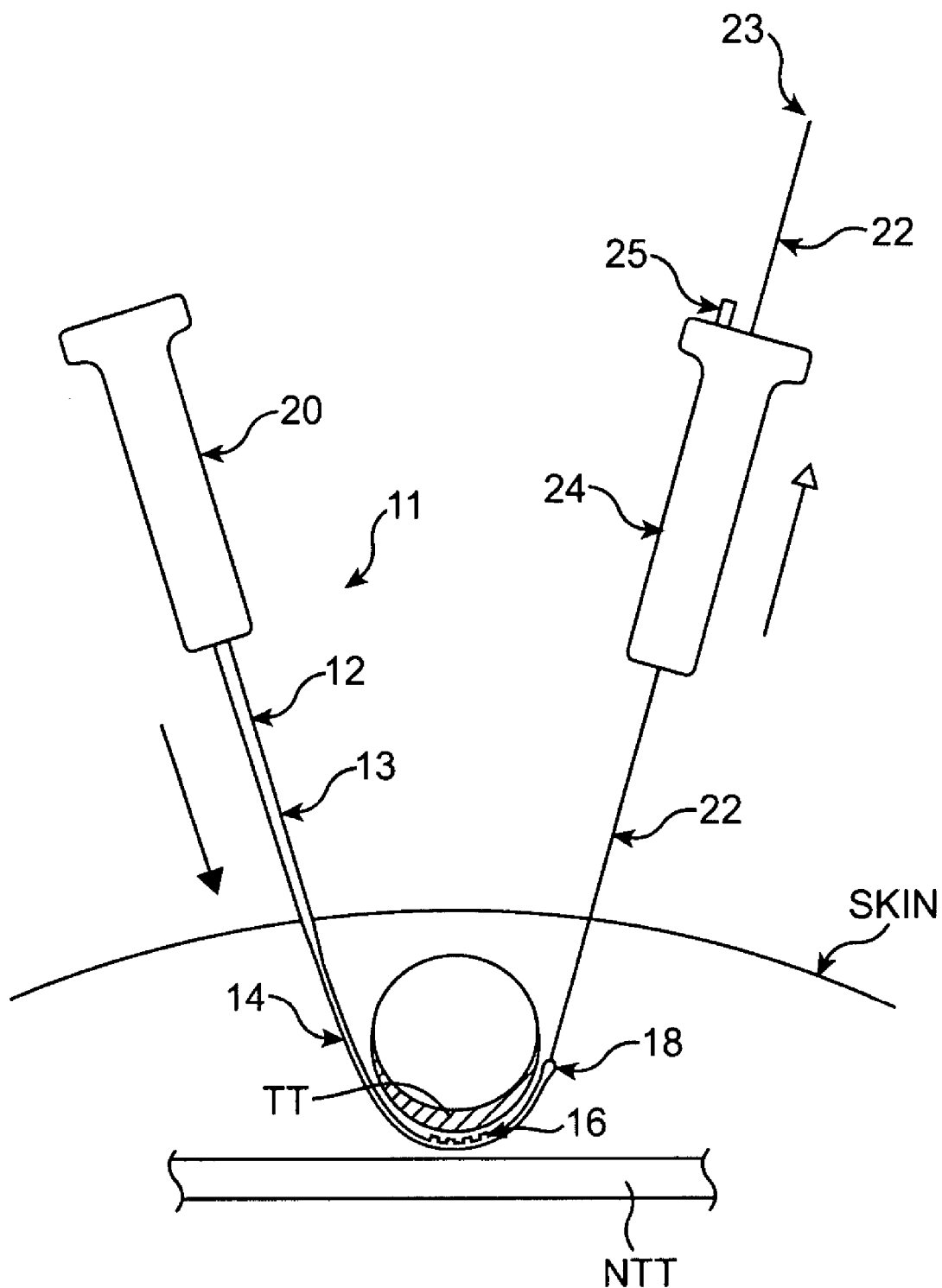

Referring to FIG. 4D, distal handle 24 may then be pulled (hollow-tipped arrow) to pull device 10 into the patient and to thus position tissue modifying members 16 in contact with target tissue TT. In some embodiments, such as when device 10 is used in a spinal procedure and passes through an intervertebral foramen, a surgeon or other physician user may use tactile feedback of device 10 passing into the foramen, such as when coupling member 18 and/or tissue modifying members 16 pass into the foramen, to determine when tissue modifying members 16 are positioned in a desired location relative to target tissue TT. Alternatively or additionally, a surgeon may confirm that a desired placement has been achieved by using radiographic imaging, such as fluoroscopy, direct visualization, such as in an open surgical case, or a combination of multiple methods.

In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

Figure 4E:
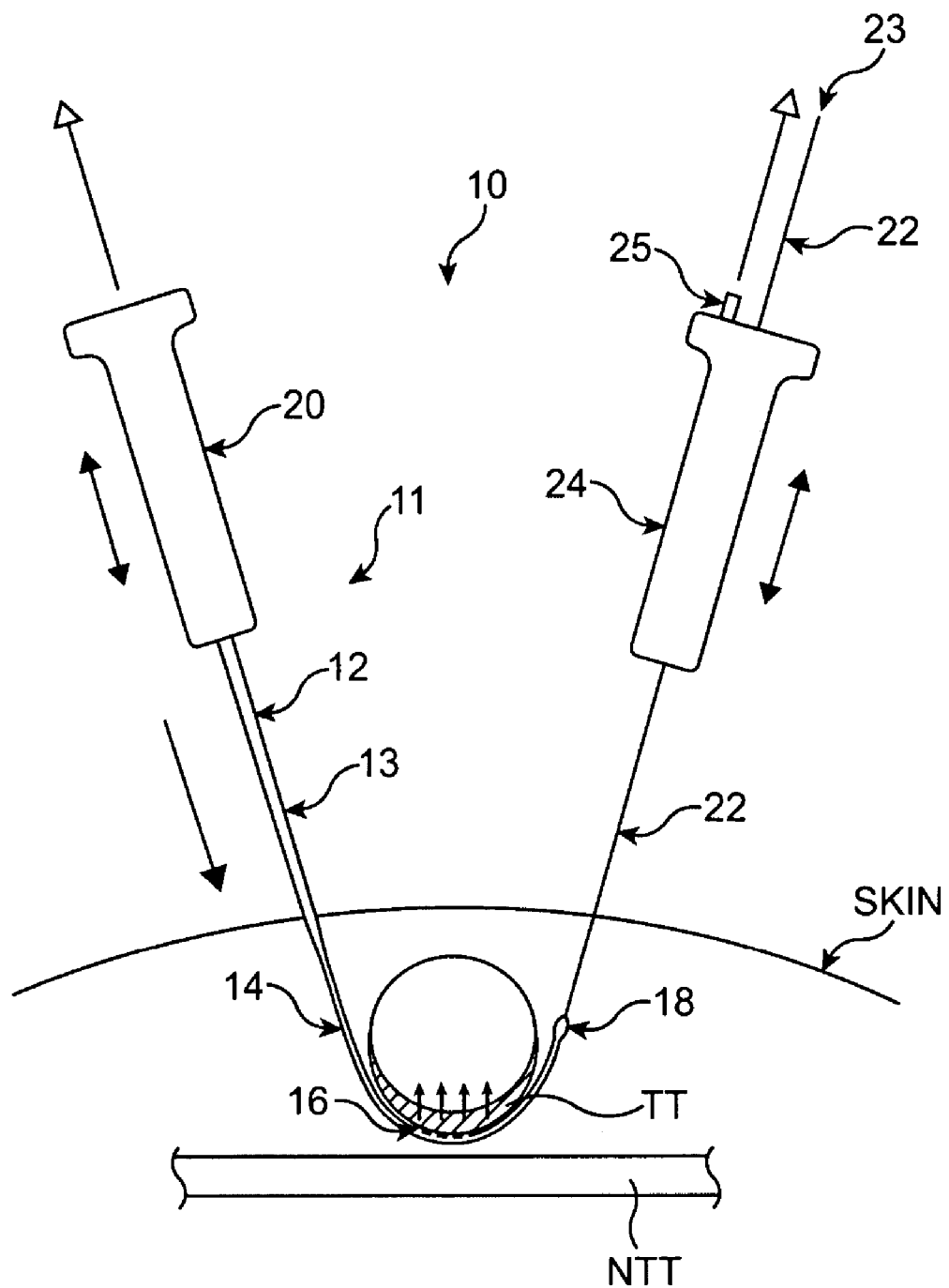

As shown in FIG. 4E, once tissue modifying members 16 are positioned as desired, relative to target tissue TT, proximal handle 20 and guidewire handle 24 may be pulled (hollow-tipped arrows) to urge tissue modifying members 16 against target tissue TT (solid-tipped arrows). While maintaining pulling/tensioning force, handles 20, 24 may be used to reciprocate device 10 back and forth (solid-tipped, double-headed arrows) to remove target tissue TT. During a procedure, rigid proximal shaft portion 13 may be used to help steer device 10, or more specifically flexible distal shaft portion 14, relative to the target TT. For example, rigid shaft portion 13 may be used to move flexible portion 14 laterally or to pivot shaft 12 about an axis located along flexible portion 14. In one embodiment, for example, rigid portion 13 may be used to manipulate flexible portion 14 within an intervertebral foramen, such as by pivoting shaft 12 or moving flexible portion 14 laterally in a caudal and/or cephalad direction, relative to the patient. The rigidity of rigid proximal shaft portion 13 may generally facilitate such steering, as compared to a completely flexible device.

When a desired amount of tissue is removed, device 10 may be removed from the patient, such as by detaching guidewire handle 24 from guidewire 22 and pulling proximal handle 20 to withdraw device 10 and guidewire 22 out of the patient. In some embodiments, device 10 or an additional device may be reinserted into the patient and used in a second location to remove additional tissue. For example, in a spinal stenosis treatment procedure, device 10 may be used to remove tissue from (and thus decompress) a first intervertebral foramen and then may be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

Figure 5A:
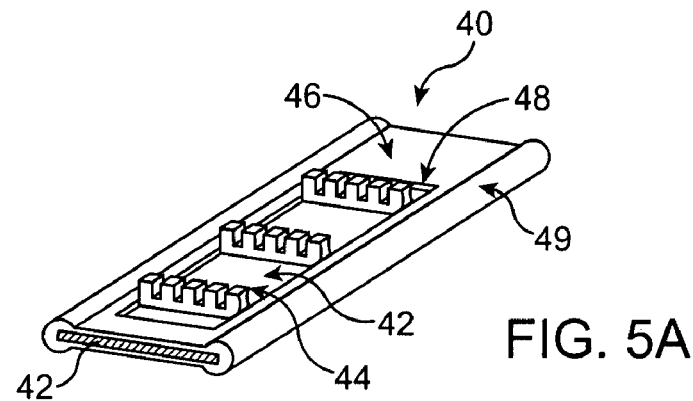
FIG. 5A is a perspective view of a flexible portion of a tissue modification device, according to one embodiment of the present invention.
Figure 5B:
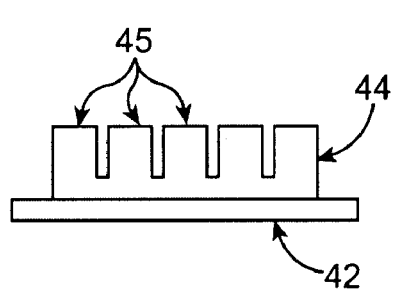
FIGS. 5B and 5C are end-on and side views of blade and substrate portions of the portion of the device of FIG. 5A.
Figure 5C:
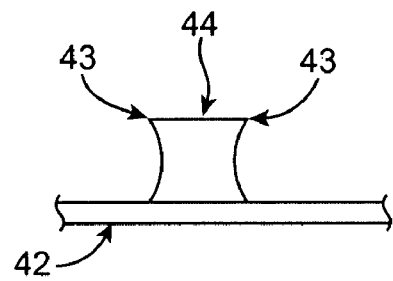

Referring now to FIGS. 5A-5C, a flexible distal portion 40 of a flexible tissue modification device is shown, in various views. In FIGS. 5A-5C and 6-25, various alternative embodiments of a flexible distal portion of a tissue modification device are shown in a generally straight configuration. However, all embodiments shown are flexible and thus may assume a curved configuration. The embodiments are shown in straight configuration for ease of illustration only.

In one embodiment, flexible distal portion 40 may include a substrate 42 (or "flexible, distal shaft portion"), multiple tissue modifying members 44 coupled with substrate 42, and an atraumatic cover 46 disposed over substrate 42 and forming an aperture 48 and atraumatic bumpers 49. FIG. 5B is an end-on view of substrate 42 and one of cutting members 44, which includes multiple teeth 45. FIG. 5C is a side view of substrate 42 and one of cutting members 44, showing that each cutting member 44 has two cutting edges 43 in this embodiment.

The embodiment of FIG. 5A includes three cutting members 44 comprising blades with multiple teeth 45 with grooves between them. Cutting members 44 in this and other embodiments may include any suitable material, such as the materials listed previously above. Any number of cutting members 44 may be used, such as from one to twenty cutting members in various embodiments. Cutting members 44 may have any suitable height and may be spaced apart from one another at any suitable distances. In one embodiment, for example, cutting members 44 may have a height designed to protrude just slightly above the height of bumpers 49, so that cutting members 44 can cut tissue but do not protrude so high as to inhibit advancement or positioning of device in the patient. In some embodiments, cutting members 44 may be constructed as separate pieces and attached to substrate 42, such as by welding or gluing with adhesive. In some embodiments, cutting members 44 may be built by stacking layers of material to one another and attaching the stacks to form one piece. Cover 46 may be coupled with substrate using any known or later invented manufacturing technique, such as thermoforming, injection molding or the like.

In various alternative embodiments of distal portion 40 of FIGS. 5A-5C, as well as in all embodiments described below and alternatives thereto, any number of cutting members 44 may be used, cutting members 44 may be made of any suitable material, and cutting members may be disposed along substrate 42 in any configuration, pattern or the like. Therefore, various alternative materials, numbers, patterns and the like of cutting members 44 will not be listed repeatedly for each alternative embodiment.

Figure 6:
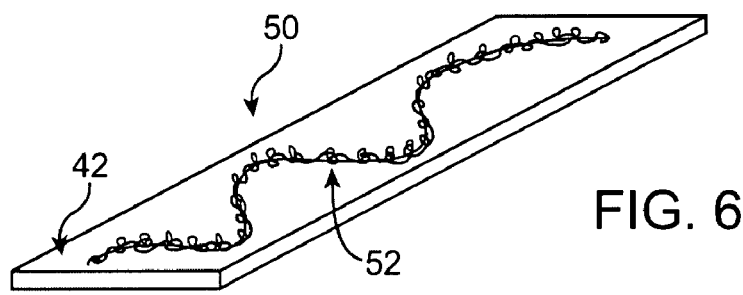
FIG. 6 is a perspective view of a portion of a flexible substrate and a wire saw tissue modifying member of a tissue modification device, according to one embodiment of the present invention.

Referring now to FIG. 6, in another embodiment, a distal portion of a flexible tissue modification device 50 may include substrate 42 and a wire saw 52 coupled with substrate 42, such as by welding. In FIG. 6, as well as in subsequent FIGS. 7-18, only a portion of each device embodiment including substrate 42 and one or more cutting members is shown, to simplify the drawing figures and description. Any of these embodiments may also include an atraumatic cover and/or other features, but for simplicity's sake, these features are not shown. Referring to the embodiment of FIG. 6, wire saw 52 may comprise any wire saw currently known or later invented, such as a Gigli saw, and may be attached to substrate 42 in any suitable pattern or configuration, such as in an S-shape pattern, as shown, or a zig-zag, straight-line or other pattern.

Figure 7:
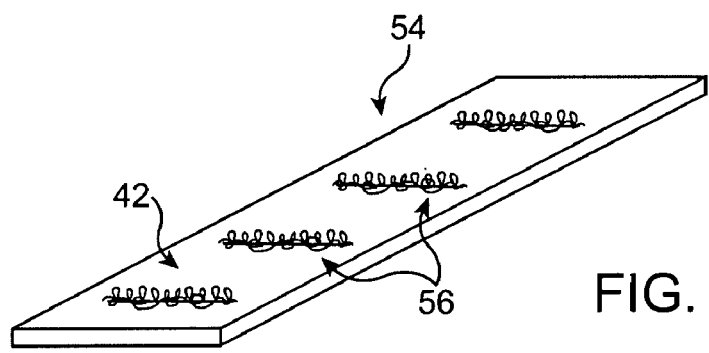
FIG. 7 is a perspective view of a portion of a flexible substrate and multiple wire saw tissue modifying members of a tissue modification device, according to an alternative embodiment of the present invention.

With reference to FIG. 7, in an alternative embodiment, a distal portion of a flexible tissue modification device 54 may include multiple pieces of wire saw 56 coupled with substrate 42. Again, these pieces of saw 56 may be attached in any pattern and by any means, such as by welding, and may comprise Gigli saw or other types of wire saw.

Figure 8:
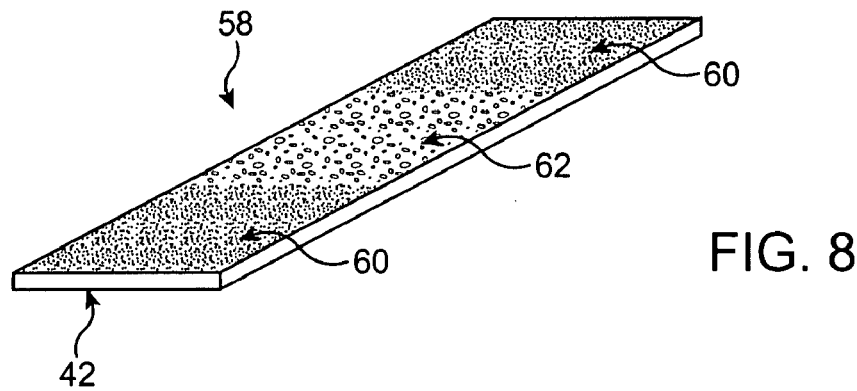
FIG. 8 is a perspective view of a portion of a flexible substrate and an abrasive surface tissue modifying member of a tissue modification device, according to an alternative embodiment of the present invention.

FIG. 8 shows a portion of another alternative embodiment of a flexible tissue modification device 58, in which abrasive materials 60, 62 are adhered to a surface of substrate. In some embodiments, only one type and/or grain of abrasive material 60 or 62 may be used, while other embodiments may include multiple types of material, multiple grains of material, or both. For example, in the embodiment shown, a finer grain of material 60 may be disposed at either end of a portion of coarser grain material 62. Such a variation in grains may provide varying degrees of tissue modification and/or the ability to remove greater amounts of tissue with a coarser grain 62 and provide a smoother finished surface to the tissue with the finer grain 60. In various embodiments, any abrasive materials 60, 62 may be used, and the materials may be adhered to substrate 42 via any method, such as adhering with adhesive or the like. One embodiment, for example, may include abrasive materials such as those described in U.S. patent application Ser. No. 10/277,776 (Pub. No. 2003/0225412), titled "Surgical Ribbon File," and filed Oct. 21, 2002, the full disclosure of which is hereby incorporated by reference. In another embodiment, substrate 42 may be treated in such a way as to have an abrasive surface, such as by sand blasting.

Figure 9:
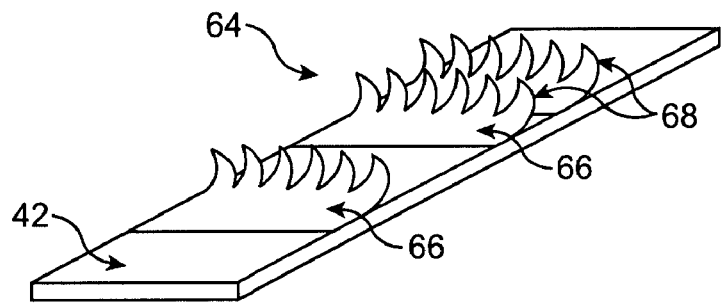
FIG. 9 is a perspective view of a portion of a flexible substrate and multiple tooth-like tissue modifying members of a tissue modification device, according to an alternative embodiment of the present invention.

Referring to FIG. 9, in another alternative embodiment, a flexible tissue modification device 64 may include multiple tissue modifying members 66, each including multiple, curved teeth 68. Cutting members 66 may be made of stainless steel or other material(s). In some embodiments, cutting members 66 may be configured to primarily cut and/or shred ligamentous tissue, such as ligamentum flavum.

Figure 10:
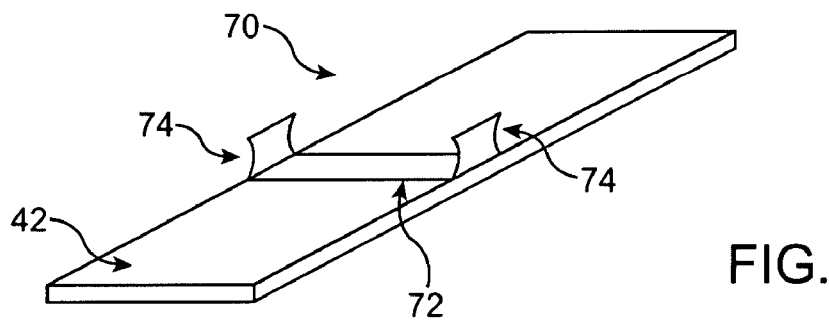
FIG. 10 is a perspective view of a portion of a flexible substrate and a two-blade tissue modifying member of a tissue modification device, according to an alternative embodiment of the present invention.

Referring to FIG. 10, in another alternative embodiment, a flexible tissue modification device 70 may include one tissue modifying member 72 with vertically oriented blades 74 at opposite ends. Blades 74 may be designed, in one embodiment, specifically for cutting or slicing ligamentous tissue, such as ligamentum flavum.

Figure 11:
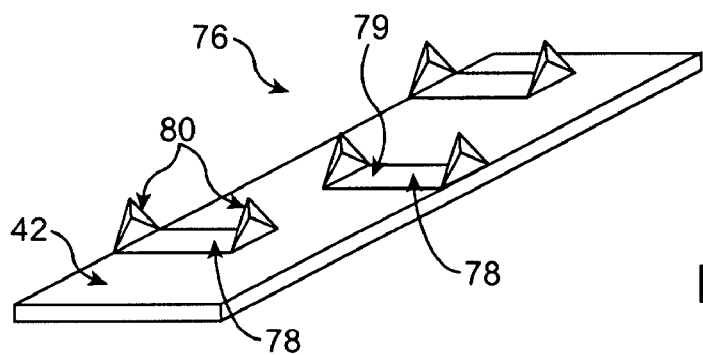
FIG. 11 is a perspective view of a portion of a flexible substrate and multiple shark-tooth-shaped tissue modifying members of a tissue modification device, according to an alternative embodiment of the present invention.

Referring to FIG. 11, in another alternative embodiment, a flexible tissue modification device 76 may include multiple tissue modifying members 78, each with vertically oriented blades 80 at opposite ends. Blades 80 may each have a shark-tooth shape, with sharp edges on opposite sides. In one embodiment, blades 80 may be designed specifically for cutting or slicing ligamentous tissue, such as ligamentum flavum. Alternatively, or additionally, blades 80 may be configured to cut bone. In one embodiment, each blade 80 may have a height approximately equal to or greater than a thickness of a ligamentum flavum. Such a blade 80 may be positioned in the spine to extend through ligamentum flavum and contact bone. When reciprocated, such a blade 80 may cut ligamentum flavum alone or may cut ligamentum flavum tissue and then, when it is removed, may also cut bone. Such a blade height and configuration may facilitate lateral steering of device 76.

Figure 12:
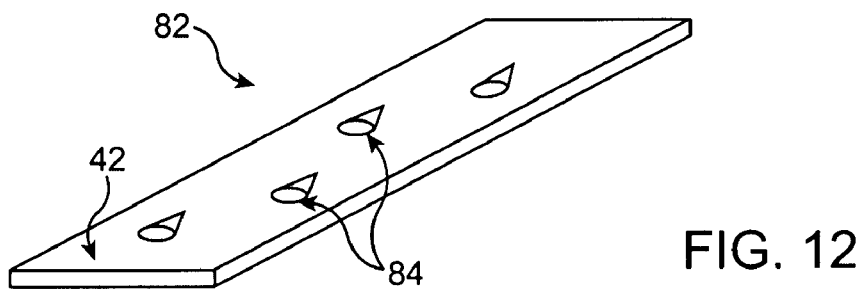
FIG. 12 is a perspective view of a portion of a flexible substrate and multiple cheese-grater-shaped tissue modifying members of a tissue modification device, according to an alternative embodiment of the present invention.

Referring to FIG. 12, in another alternative embodiment, a flexible tissue modification device 82 may include multiple tissue modifying members 84 formed as holes in substrate 42 with raised edges, such as are found on a cheese grater. The raised edges of cutting members 84 may be sharp, to provide cutting. Any number of tissue modifying members 84 may be included, they may have any desired size, and they may be formed on substrate in any pattern. In some embodiments, cut tissue may pass through the holes of cutting members 84 and thus through substrate 42. In some embodiments, a tissue capture device or member may be coupled with the back side of substrate 42 to collect cut tissue that passes through cutting members 84.

Figure 13:
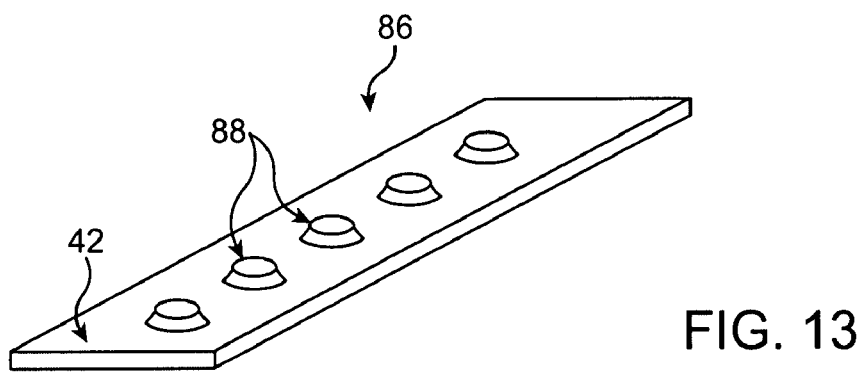
FIG. 13 is a perspective view of a portion of a flexible substrate and multiple raised tissue modifying members of a tissue modification device, according to an alternative embodiment of the present invention.

Referring to FIG. 13, in another alternative embodiment, a flexible tissue modification device 86 may include multiple tissue modifying members 88 formed as upward-facing holes in substrate 42. The raised edges of cutting members 88 may be sharpened, to provide cutting. Any number of tissue modifying members 88 may be included. In some embodiments, cut tissue may pass through the holes of cutting members 88 and thus through substrate 42. In some embodiments, a tissue capture device or member may be coupled with the back side of substrate to collect cut tissue that passes through cutting members 88.

Figure 14:
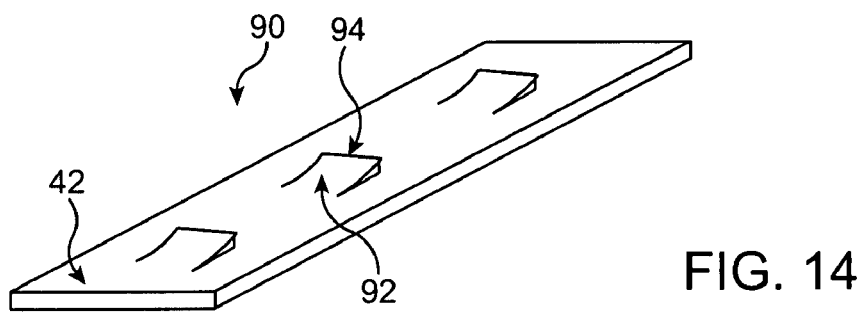
FIG. 14 is a perspective view of a portion of a flexible substrate and multiple raised-flap tissue modifying members of a tissue modification device, according to an alternative embodiment of the present invention.

Referring to FIG. 14, in another alternative embodiment, a flexible tissue modification device 90 may include multiple tissue modifying members 92 formed as raised flaps in substrate 42, with each flap 92 including a sharpened cutting edge 94. Any number of tissue modifying members 92 may be included. In some embodiments, cut tissue may pass underneath the flap-like cutting members 92 and thus through substrate 42. In some embodiments, a tissue capture device or member may be coupled with the back side of substrate to collect cut tissue that passes through cutting members 92.

Figure 15:
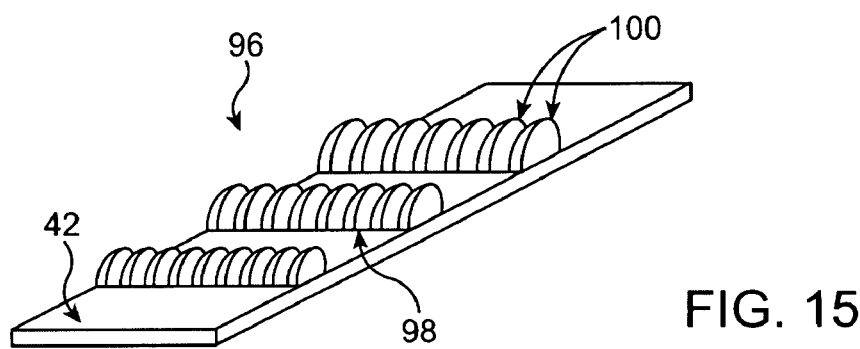
FIG. 15 is a perspective view of a portion of a flexible substrate and multiple rounded tissue modifying members of a tissue modification device, according to an alternative embodiment of the present invention.

Referring to FIG. 15, in another alternative embodiment, a flexible tissue modification device 96 may include multiple tissue modifying members 98 formed as rounded cutting devices coupled with substrate 42. In one embodiment, each cutting member 98 may include multiple ridges, divided by grooves. In one embodiment, cutting members 98 may have a spiral or screw-like configuration.

Figure 16:
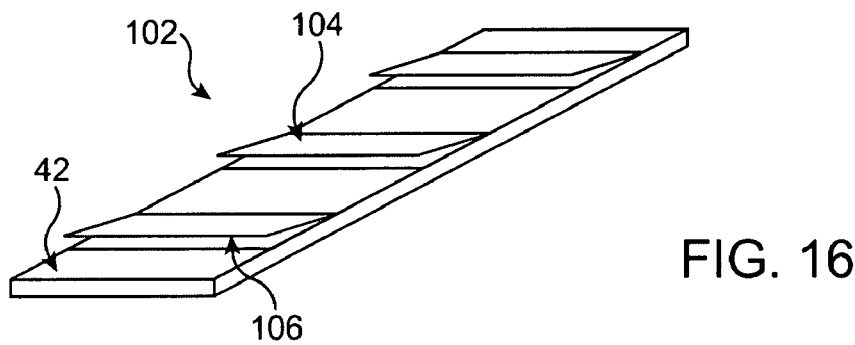
FIG. 16 is a perspective view of a portion of a flexible substrate and multiple raised-flap tissue modifying members of a tissue modification device, according to an alternative embodiment of the present invention.

Referring to FIG. 16, in another alternative embodiment, a flexible tissue modification device 102 may include multiple tissue modifying members 104 comprising thin, flap-like blades coupled with substrate 42, each cutting member 104 including a sharp blade edge 106. Any number, size and configuration of blades may be used.

Figure 17:
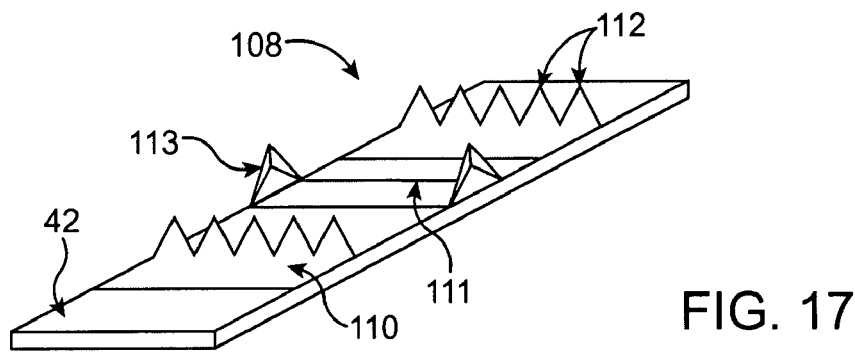
FIG. 17 is a perspective view of a portion of a flexible substrate and multiple, differently shaped tissue modifying members of a tissue modification device, according to an alternative embodiment of the present invention.

Referring to FIG. 17, in another alternative embodiment, a flexible tissue modification device 108 may include multiple different types of tissue modifying members 110, 111. For example, one embodiment may include one or more jagged tissue cutters 110 each having multiple, triangular, raised teeth 112, and one or more bladed tissue cutters 111, each having multiple blades 113. Teeth 112 and/or blades 113 may be configured specifically to cut ligamentum flavum tissue, bone, or both, in various embodiments.

Figure 18:
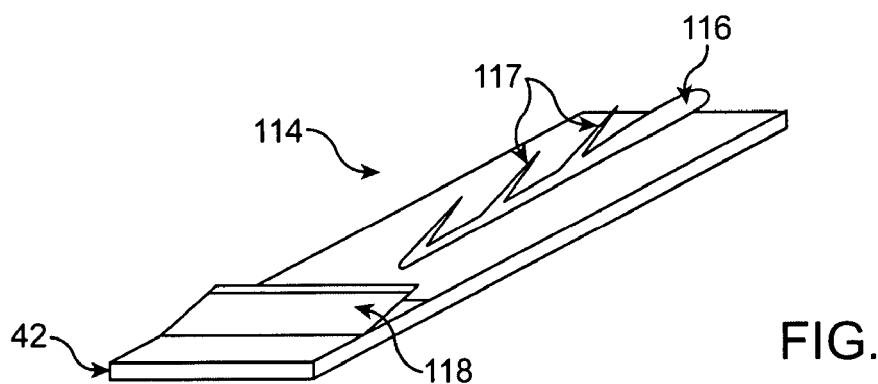
FIG. 18 is a perspective view of a portion of a flexible substrate and barbed-hook and raised-flap tissue modifying members of a tissue modification device, according to an alternative embodiment of the present invention.

Referring to FIG. 18, in another alternative embodiment, a flexible tissue modification device 114 may include substrate 42, a tissue engaging member 116 including multiple barbs 117 (or hooks, needles or the like), and one or more tissue cutting members 118, such as a raised blade. In various embodiments, tissue engaging member 116 may be configured to hook, snag, grab or otherwise engage soft tissue, such as ligamentum flavum, and pull or stretch such tissue as it is pulled or pushed across the tissue. Tissue cutting member 118 may follow behind tissue engaging member 116 and cut the stretched/pulled tissue. Such stretching or pulling of tissue before cutting may facilitate or enhance tissue cutting.

Figure 19:
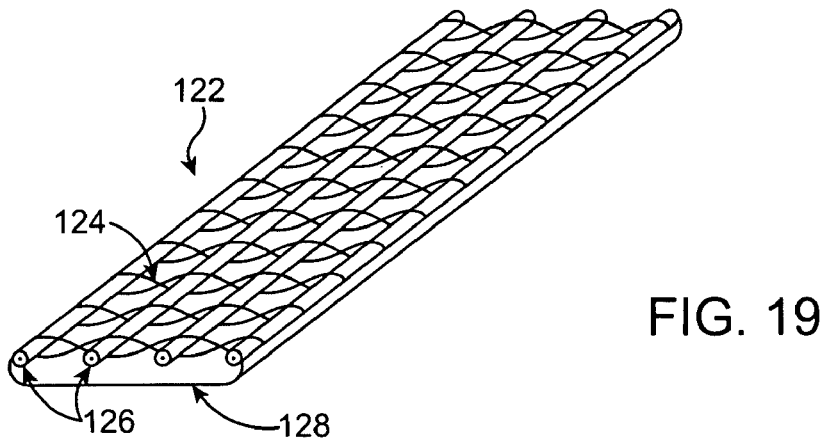
FIG. 19 is a perspective view of a portion of a wire mesh flexible tissue modification device, according to an alternative embodiment of the present invention.

Referring to FIG. 19, in another alternative embodiment, a flexible tissue modification device 122 may include a wire mesh 124 coupled with multiple supporting structures 126 and an atraumatic material 128 on one side. All components may be made of any suitable material, such as those listed previously.

Figure 20:
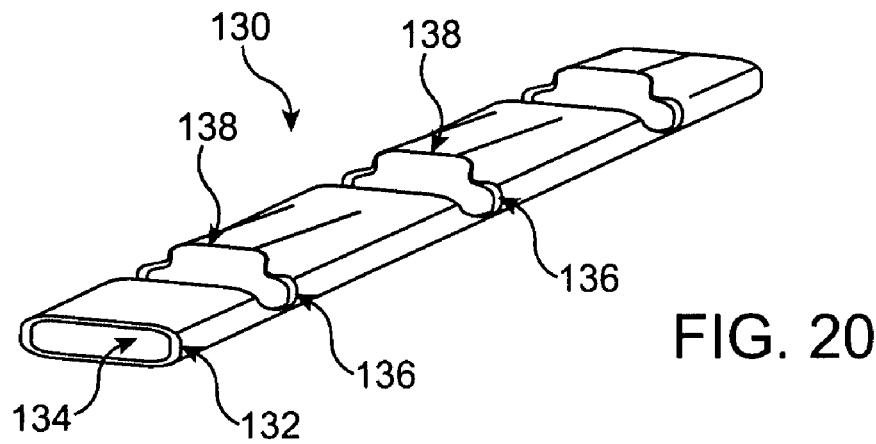
FIG. 20 is a perspective view of a portion of a flattened, hollow, flexible tissue modification device, according to an alternative embodiment of the present invention.

Referring to FIG. 20, in another alternative embodiment, a flexible tissue modification device 130 may comprise a hollow, flattened shaft 132, having central chamber or lumen 134, into which multiple grooves 136 may be cut. An edge of each groove 136 may be raised and sharpened to form a blade edge 138, thus forming a multiple, bladed tissue modifying members. Tissue cut by blades 138 may pass under blades 138 to collect within lumen 134 and may thus be transported out of the patient.

Figure 21:
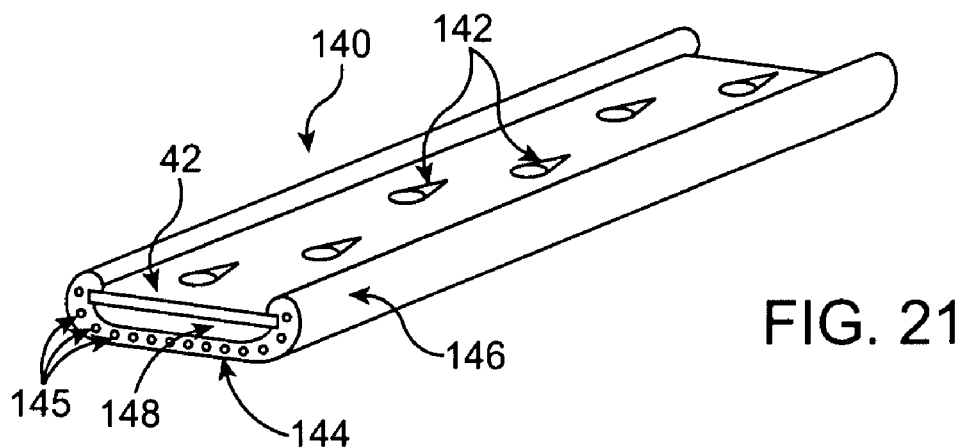
FIG. 21 is a perspective view of a portion of a flexible substrate and cheese-grater-shaped tissue modifying members coupled with a tissue capture member of a tissue modification device, according to an alternative embodiment of the present invention.

Referring to FIG. 21, in another alternative embodiment, a flexible tissue modification device 140 may include multiple tissue modifying members 142 formed as holes in substrate 42 with raised edges, such as are found on a cheese grater. The raised edges of cutting members 142 may be sharpened, to provide cutting. Any number of tissue modifying members 142 may be included. In some embodiments, cut tissue may pass through the holes of cutting members 142 and thus through substrate 42. In some embodiments, a tissue collection member 144, forming a tissue collection chamber 148, may be coupled with the back side of substrate 42 to collect cut tissue that passes through cutting members 142. Tissue collection member 144 may also serve as an atraumatic tissue protection member and may include, for example, side bumpers 146 to avoid damaging non-target tissue with sharp edges of device 140. In some embodiments, tissue collection member 144 may be strengthened by multiple fibers 145, such as wires or carbon fibers.

Figure 22:
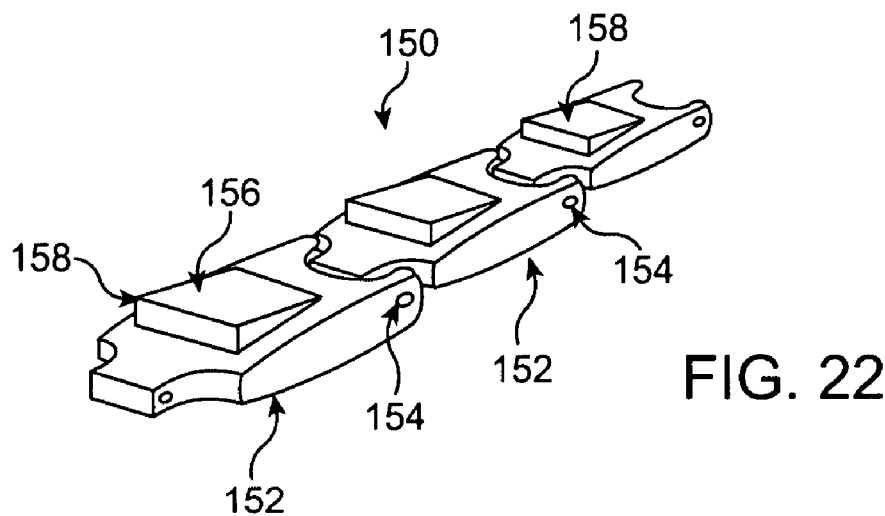
FIG. 22 is a perspective view of a portion of a moveable-link flexible tissue modification device, according to an alternative embodiment of the present invention.

Referring to FIG. 22, in another alternative embodiment, a flexible tissue modification device 150 may include multiple sections 152 linked together via linkages 154 to form a flexible device configuration analogous to that of some watch bands. A tissue modifying member 156 having a cutting edge 158 may be disposed on one side of each section 152 to cut tissue.

In various embodiments, any given flexible tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. For example, many of the devices described above may also optionally be loaded with a drug, bone wax, gel foam, or the like, which may be deposited during a tissue modification procedure. Any suitable drug may be delivered via the devices in various embodiments, such as but not limited to thrombin, NSAID, local anesthetic or opioid. In some embodiments, devices may also deliver an implant, such as a stent-like implant for maintaining patency of decompressed intervertebral foramen, a rivet, staple or similar device for retracting ligamentum flavum tissue, a tissue dressing, or the like. In some embodiments, devices may cool or freeze tissue for analgesia or to change the tissue's modulus of elasticity to facilitate tissue modification. Some embodiments of devices may also include a visualization and/or diagnostic component, such as an ultrasound, MRI, reflectance spectroscopy, fiber optic, endoscope, charge-coupled device (CCD), complementary metal-oxide semiconductor (CMOS) or other device.

Any of the devices described herein may also optionally include one or more components for neural identification and/or localization. For example, in some embodiments, a flexible tissue modification device may include one or more nerve stimulation electrodes on a backside or underside of the device (i.e., a side designed to be atraumatic and face non-target tissue). The electrode(s) may be used to confirm that the atraumatic side of the device is in contact with non-target neural tissue, thus also confirming that the tissue modification members of the device are facing target tissue. In some embodiments, the devices may also include one or more electrodes on an upper surface, at or near the tissue modification members, to further confirm a desired placement of the device. For further description of such neural localization devices and methods, reference may be made to U.S. patent application Ser. No. 11/457,416, which was previously incorporated by reference.

Figure 23:
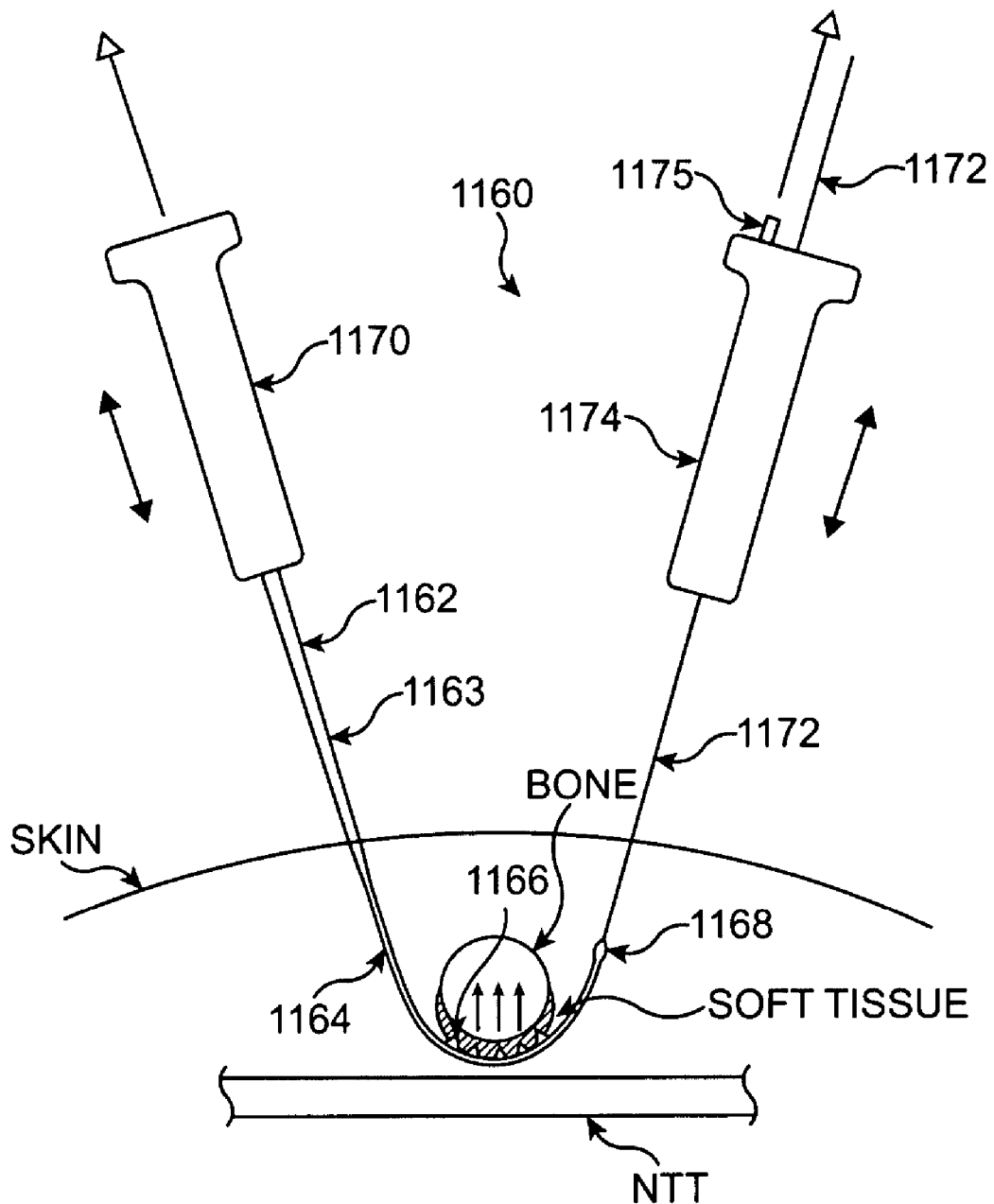
FIG. 23 is a side view of a tissue modification device in a position for performing a tissue modification procedure, showing a generic bone, soft tissue and non-target tissue, according to one embodiment of the present invention.

With reference now to FIG. 23, in another alternative embodiment, a tissue modification device 1160 may suitably include a proximal handle 1170 coupled with an elongate body 1162 (or "shaft") having a proximal, rigid shaft portion 1163 and a distal, flexible portion 1164 from which multiple blades 1166 may extend. A guidewire coupler 1168 may be formed in (or attached to) flexible portion 1164 at or near its distal end for coupling with a guidewire 1172, which in turn may be coupled with a guidewire handle 1174 (or "distal handle"). Distal handle 1174 may include a tightening lever 1175 for tightening handle 1174 around guidewire 1172. In one embodiment, device 1160 may have many of the characteristics and be used in much the same way as embodiments described above.

In FIG. 23, device 1160 is shown passing into a patient, along a curved path between a generic soft tissue/bone combination and nearby non-target tissue NTT, and back out of the patient. In one embodiment, device 1160 may be passed into a patient, through an intervertebral space of the patient's spine (between ligamentum flavum and neural/neurovascular tissue), and back out of the patient, as described in detail above with reference to alternative embodiments. Once device 1160 is in place for modifying a target tissue, such as soft tissue and/or bone, handles 1170, 1174 may be pulled (hollow-tipped arrows) to apply force and thus urge blades 1166 into soft tissue (single-headed, solid-tipped arrows).

Device 1160 may then be reciprocated (double-headed, solid-tipped arrows), while maintaining some or all of the pulling force, to remove or otherwise modify the target soft tissue and/or bone. As mentioned previously, before reciprocating device 1160 to remove tissue, in some embodiments the device may be used to stimulate nearby nerve tissue, such as with an electrode coupled with the back and/or front side(s) of flexible portion 1164. Such nerve stimulation may help confirm that device 1160 has been placed in a desired location for treatment and may be monitored using electromyography (EMG), visual observation of muscle twitch and/or the like.

Figure 24:
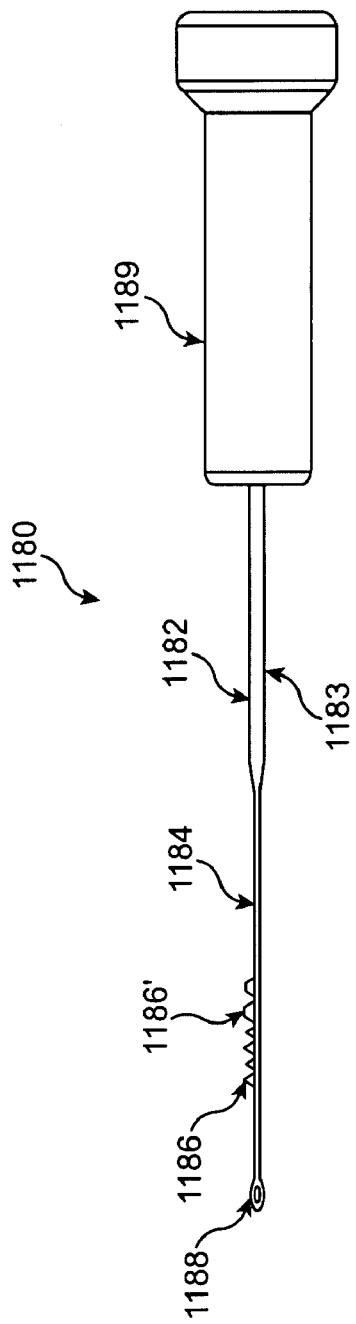
FIG. 24 is a side view of a tissue modification device with vertically oriented blades, according to one embodiment of the present invention.

Referring to FIG. 24, in one embodiment a tissue modification device 1180 may include a proximal handle 1189 coupled with one end of an elongate body 1182, which includes a proximal rigid shaft portion 1183 and a distal flexible portion 1184. Multiple blades 1186, 1186' extend from a first side of flexible portion 1184, while a second side approximately opposite the first side is substantially atraumatic to inhibit damage to non-target tissues during a tissue modification procedure. Flexible portion 1184 may also include a guidewire coupler 1188 at its distal end. In various embodiments, a suitable combination of blades 1186, 1186' may be included on a given tissue modification device. For example, device 1180 includes four pointed-tip blades 1186 and two flat-top blades 1186'. Various blades may be configured to perform one or more of a number of functions. For example, pointed-tip blades 1186 may be ideal for cutting through soft tissue and bone, while flat-top blades 1186' may be best for cutting through soft tissue and riding along a bone surface to help steer or guide device 1180. In some embodiments, all blades on a device may be configured for optimal soft tissue cutting, such as cutting of ligamentum flavum tissue in the spine, while in other embodiments all blades may be configured for optimal bone cutting, such as vertebral bone. Other alternative embodiments may include a combination of blade shapes and configurations to provide multiple different types of cutting. Further discussion of blades combinations and configurations are included in application Ser. No. 11/687,558, filed concurrently herewith and entitled "Flexible Tissue Removal Devices and Methods" the full disclosure of which is incorporated herein by reference.

Figure 25:
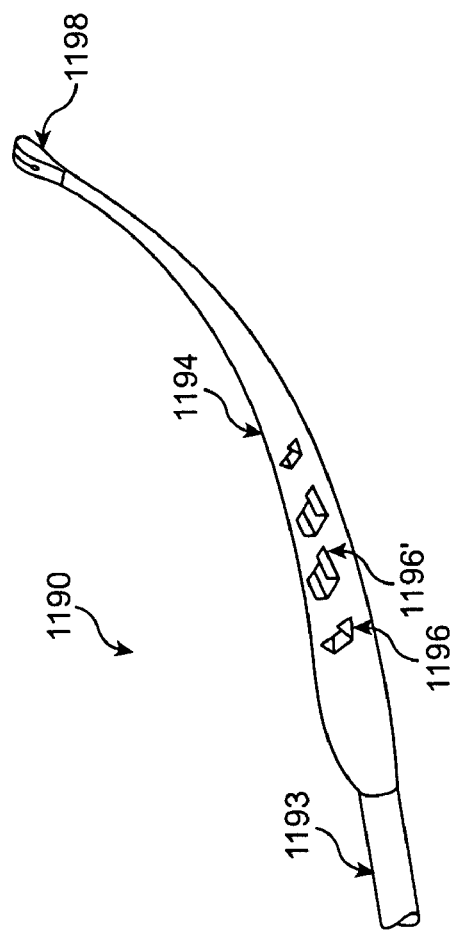
FIG. 25 is a perspective view of a flexible portion of a tissue modification device with vertically oriented blades, according to one embodiment of the present invention.

With reference now to FIG. 25, a perspective view of a portion of an alternative embodiment of a tissue modification device 1190 shows a rigid shaft portion 1193 extending to a flexible portion 1194 with pointed-tip blades 196, flat-top blades 1196', and a guidewire coupler 1198. In the embodiment shown, and as is described in further detail below in relation to another embodiment, some or all blades 1196' may be angled, relative to a longitudinal axis of the elongate body and flexible portion 1194 of device 1190. Angling blades 1196' may cause or facilitate lateral movement of device 1190 along a target tissue as device 1190 is reciprocated back and forth to modify the tissue, thus providing for wider or more complete tissue modification/removal.

Figure 26A:
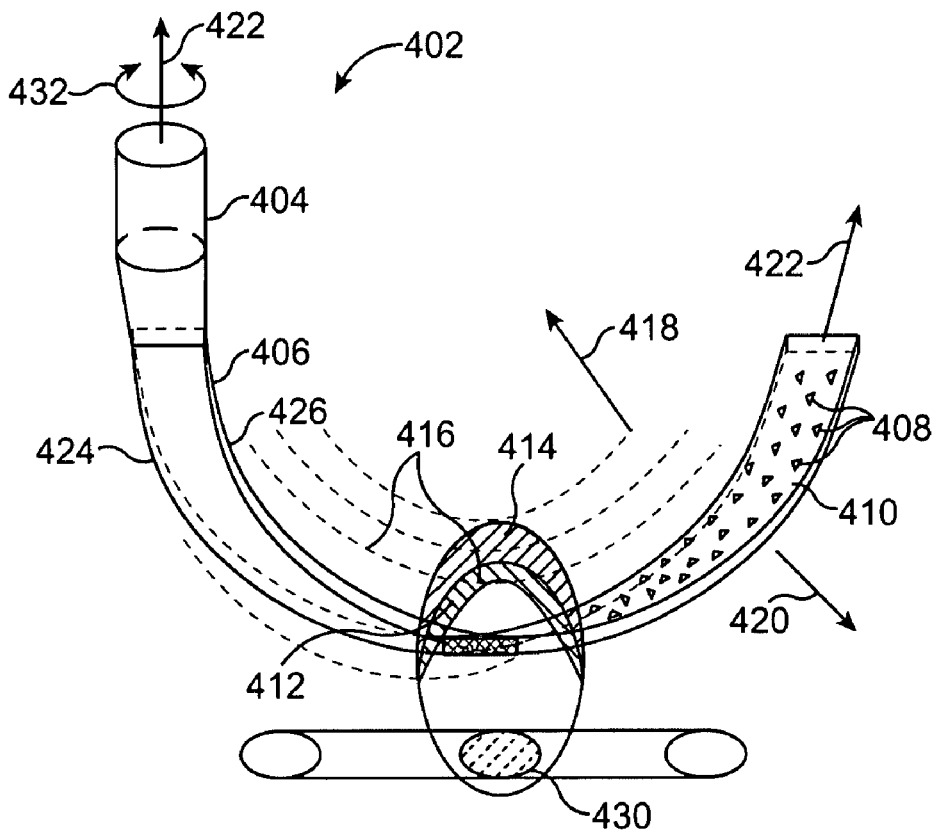
FIGS. 26A and 26B illustrate how tension in a flexible portion of a tissue modification device bent over a target tissue can urge blades or other tissue modification devices into the target tissue, and how torque to the rigid portion of the tissue modification device can maintain or alter an orientation of the flexible member and inhibit flipping of the flexible member.
Figure 26B:
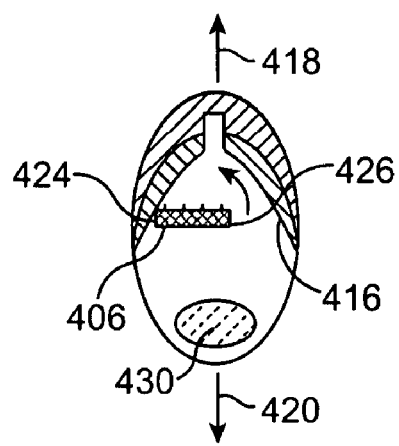

Referring now to FIGS. 26A and 26B, a tissue modification device 402 has a rigid proximal shaft portion 404 from which a flexible portion 406 extends axially. A plurality of tissue modification elements in the form of blades 408 extend from a first surface 410 of flexible portion 406, as described above. Flexible portion 406 is advanced into a patient body so that first surface 410 is bent over a target tissue, with the target tissue here comprising both ligament 412 and bone 414. First surface 410 of flexible portion 406 is wrapped over an at least partially convex surface 416, with the convexity of the surface defining an inward orientation 418 and an outward orientation 420 (see FIG. 40B). Hence, axial tension 422 on the flexible portion 406 causes the first surface 410 to move inwardly toward the target tissue 412, 414.

Referring still to FIGS. 26A and 26B, the surface 416 of the target tissue need not, and often will not, be substantially cylindrical, but will often instead have portions that are more inward 418, and other portions that are more outward 420. For example, a first portion or region of the surface 416 adjacent a first edge 424 of flexible portion 406 may be significantly more outward 420 than a region of the surface that is adjacent an opposed edge 426 and engagement between the flexible portion and tissue surface. As a result of the axial tension 422 in the flexible portion 406, this difference can cause the flexible portion to rotate about its central axis. Continued reciprocation of the flexible portion when its rotational orientation is not adequately controlled could cause an edge 426 of the flexible portion to cut laterally into target tissues as illustrated in FIG. 26B, or even inadvertent flipping of the flexible portion which might expose non-target tissue 430 to damage from the cutting blades along first surface 410, rather than effecting controlled volumetric removal of the target tissue.

To inhibit uncontrolled rotation of the flexible portion 406, the rigid shaft of proximal portion 404 significantly improves the control over both the orientation and position of the flexible portion, in part by transmitting torque 432 from the proximal handle to the treatment site within the patient. By rotating (or restraining) the proximal handle about the axis of the shaft, torque is transmitted down the shaft and to the flexible portion adjacent the target tissue. The torque can be transmitted so as to inhibit rolling or flipping of the flexible portion, and can also be used to intentionally alter an orientation of the flexible portion and tissue modifying members. The proximal handle and/or proximal portion may have an asymmetric shape or some asymmetric indicia that identifies the orientation of the tissue modifying members to enhance the physician's control over the orientation of tissue being modified and/or removed.

Figure 27A:
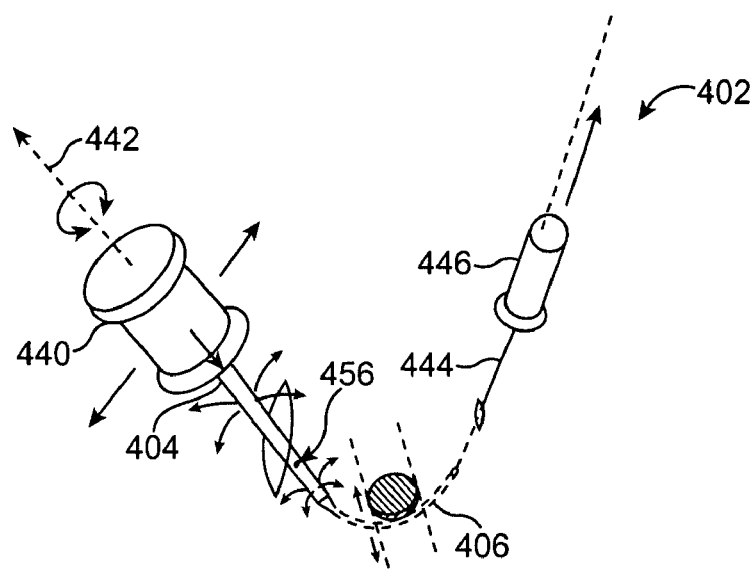
FIG. 27A is a perspective view schematically illustrating shifting of the flexible member laterally along a target tissue by laterally translating the proximal rigid portion, and/or by pivoting the rigid portion about tissues along the site of insertion.
Figure 27B:
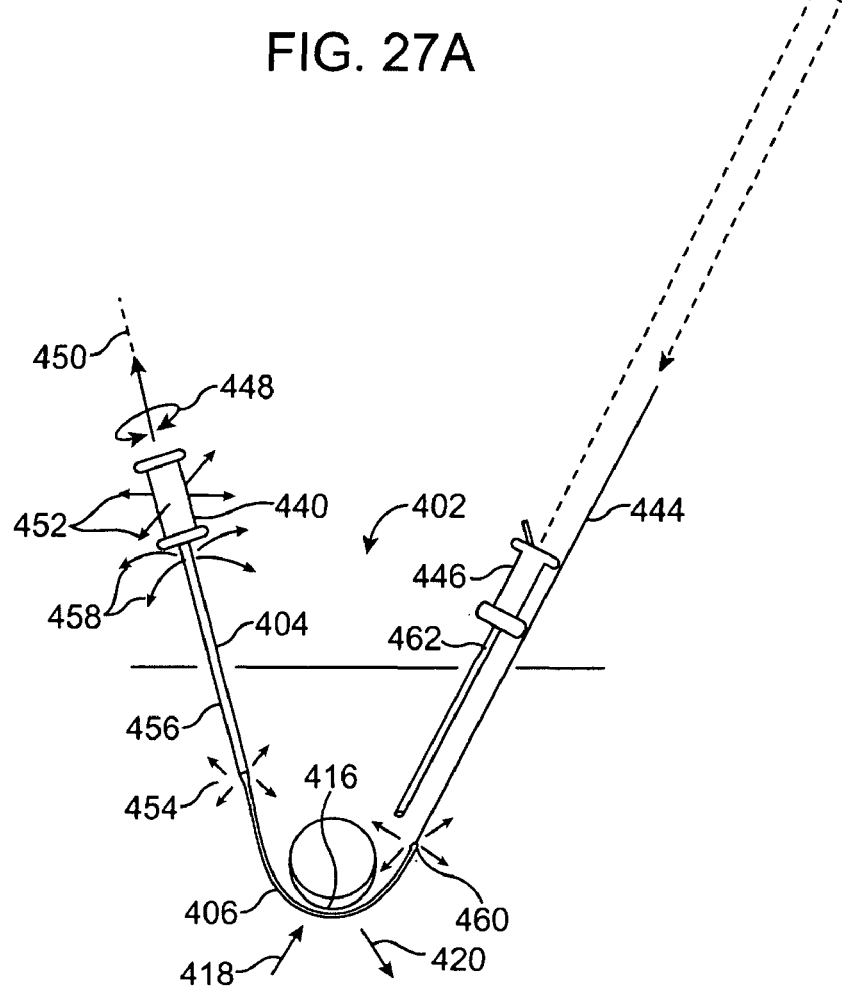
FIG. 27B schematically illustrates lateral translation and pivoting of the rigid portion to effect shifting of the flexible portion relative to the target tissue, and also schematically illustrates an optional rigid tubular shaft coupled to a distal handle to similarly allow shifting of the distal end of the flexible portion and provide enhanced control over target tissue remodeling and/or removal.

Referring now to FIGS. 27A and 27B, additional aspects of the structure and use of rigid shaft proximal portion 404 to control the location and orientation of distal flexible portion 406 can be understood. As generally described above, tissue modification tool 402 is generally positioned for use with rigid portion 404 extending a proximal handle 440 through an open or minimally invasive surgical axis site to flexible portion 406, with the flexible portion often extending distally from an axis 442 of the proximal portion. The distal flexible portion 406 also has a central axis which extends around a target tissue to a distal end that is coupled to a guidewire 444 extending out of the patient, with a distal handle 446 being axially affixable to the guidewire so that tension can be applied to the flexible portion 406 by pulling upward on the proximal and distal handles 440, 446.

As described above, torqueing the shaft of rigid portion 404 about it's axis using handle 440 (as schematically illustrated by arrows 448) can help to orient the tissue treatment member(s) along the first surface 410 of flexible portion 406 toward a target region of the target tissue. Additionally, it will often be desirable to shift flexible portion 406 laterally relative to its central axis, that is, into and/or out of the illustration of FIG. 27B. Handle 440 can be used to help move flexible portion 406 using one or both of two techniques. First, handle 440 can be pushed laterally relative to the axis 450 of the rigid proximal shaft portion 404 as illustrated by arrows 452. Where handle 440 laterally translates the shaft without rotating of the shaft, end 454 of rigid portion 404 may also translate laterally, thereby laterally shifting the flexible portion 406. Alternatively, handle 440 may be used to pivot the rigid portion 404 about an effective pivot point 456 (as schematically illustrated by curving arrows 458), similarly effecting lateral movement of the end 454 of the rigid portion within the patient. Some combination of lateral movement of the overall rigid portion 404 will often be combined with some pivoting of the rigid portion. The pivot point 456 is not necessarily at a fixed location in space, and may move somewhat as the tissues adjacent the tissue modification tool 402 are displaced and/or compressed.

As described above, guidewire 444 advantageously allows tension to be applied to a distal end 460 of flexible portion 406, optionally allowing the flexible portion to be shifted and/or positioned along its curving access for treatment of a target tissue, as well as allowing distraction of target tissues, reciprocation of the tissue modification elements and flexible portion against a target tissue, and the like. To enhance lateral and rotational control over the flexible portion 406, and particularly the length of the flexible portion close to its distal end 460, a second rigid shaft 462 may be affixed to distal handle 446. The second shaft 462 may have a central lumen that receives guidewire 444 therethrough. Second shaft 462 may then be manipulated as described above regarding the rigid portion 404, allowing the distal end 460 of the flexible portion to be shifted in coordination with the shifting effected by the rigid portion 404. This may enhance overall control over the lateral movement of flexible portion, optionally using the pivoting and/or lateral movement techniques described above. The second rigid shaft 462 will often have a distal end with a profile suitable for advancing distally over guidewire 44 toward the target tissue, and may also torquably engage the distal end of flexible portion 406 so as to allow the distal end to be torqued about the longitudinal axis of the flexible portion and guidewire (such as by providing a slot in the inserted end of second shaft 462 to torquably receive the distal end of the flexible portion).

Referring now to FIGS. 28A-28E, it will often be desirable to remove target tissue from a tissue region 1259 which is wider than an adjacent tissue modification device 1260. Additionally, it may be desirable to reorient the tissue modification members carried by a flexible portion of a tissue modification device 1260 so as to treat portions of the target tissue that are at different angles. As described above, tensioning of tissue modification device 1260 using the proximal and distal handles can urge the tissue modifying members toward a first region of the target tissue, such as the region being engaged by blades 1262, 1262' in FIG. 28B. As this tissue is removed, the tension will tend to keep the tissue modification device 1260 at the removed tissue location. Optionally, the orientation of the tissue modification device 1260 may be rotated about a central axis of the flexible portion of the tissue modification device by rotation of rigid portion 404 (see FIGS. 26A, 27A), resulting in lateral rotation of the flexible portion and tissue modification elements carried thereby in a counter-clockwise direction (see FIG. 28C) wherein a clockwise direction (see FIG. 28D). Additionally, lateral translation and/or pivoting of the rigid portion 404 about pivot point 456 may be used to laterally shift or translate the tissue treatment device 1260.

Lateral shifting of the flexible portion may be facilitated (for example) by including tissue modification devices or blades having sufficient length to extend through ligament target tissue such as the ligamentum flavum, and by including tips on at least some of the tissue modification devices or blades that are large enough to avoid penetrating into underlying bone. This may allow the flexible substrate to ride over the tough ligament, facilitating lateral movement of the outermost blades into target ligament tissues. Lateral shifting of the flexible portion may also be facilitated by a flexible substrate structure which is relatively stiff in one lateral orientation (specifically, along the major surfaces) and more flexible in another lateral orientation (transverse to the major surfaces, so as to allow the flexible member to bend over the target tissue with a major surface oriented toward the target tissue). Advantageously, such selective lateral flexibility and lateral stiffness can be readily provided by a thin, flat substrate having a cross-section that includes a much larger moment in one orientation (for example, bending in the plane of the major surfaces) than another (for example, bending in the plane of the smaller edges).

Figure 28A:
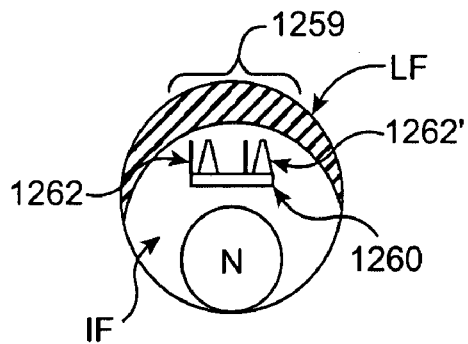
FIGS. 28A-28E are end-on views of a flexible portion of a tissue modification device with vertically oriented blades, demonstrating a method for shifting the device back and forth laterally in an intervertebral foramen, according to one embodiment of the present invention.

Still with reference now to FIGS. 28A-28E, a method according to one additional embodiment can be understood for removing tissue using a tissue modification device 1260. FIG. 28A is an end-on, diagrammatic representation of an intervertebral foramen IF, showing vertebral bone, ligamentum flavum LF and nerve root N, with device 1260 passing through the foramen IF between nerve root N and ligamentum flavum LF. Device 1260 may have some blades 1262 oriented at approximately a 0 degree angle relative to the longitudinal axis of device 1260, while other blades 1262' may be angled, relative to the longitudinal axis.

Figure 28B:
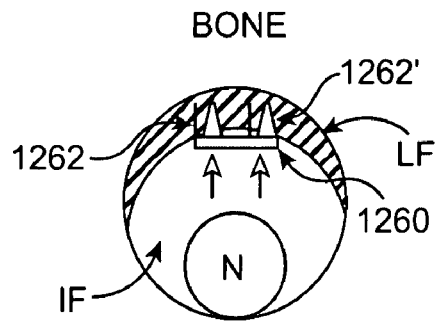

In FIG. 28B, device 1260 has been pulled upward (hollow-tipped arrows) to urge blades 1262, 1262' into ligamentum flavum LF so that at least one of blades 1262, 1262' contacts vertebral bone. In some embodiments, some or all of blades 1262, 1262' may have a height approximating a thickness of an average ligamentum flavum LF.

Figure 28C:
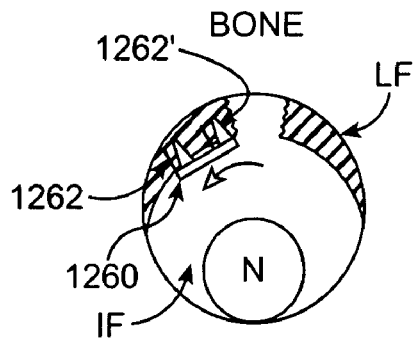

Referring to FIG. 28C, when device 1260 is reciprocated back and forth along its long axis, ligamentum flavum LF tissue is removed in one area of the intervertebral foramen IF. As device 1260 is reciprocated, angled blades 1262' may steer or guide device 1260 laterally in the intervertebral foramen IF (hollow-tipped arrow). In some embodiments, for example, device 1260 may steer to one side when the device is pulled in one direction and steer to the other side when the device is pulled in the opposite direction.

Figure 28D:
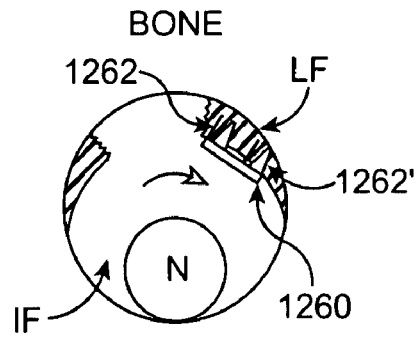

In FIG. 28D, device 1260 has moved toward the opposite lateral side of the intervertebral foramen IF (hollow-tipped arrow) to remove additional ligamentum flavum LF tissue. In some embodiments, any or all blades 1262, 1262' of device 1260 may have flat tops, which may help blades 1262, 1262' to slide or "skate" across the surface of bone as device 1260 is reciprocated to cut through soft tissue. This sliding or skating motion may also help device 1260 move from side to side within the intervertebral foramen IF.

Figure 28E:
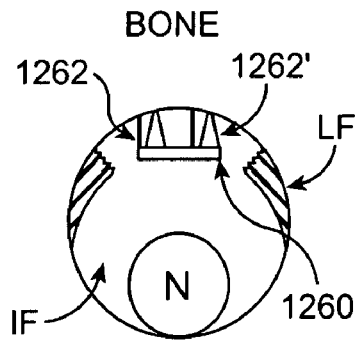
Figure 29:
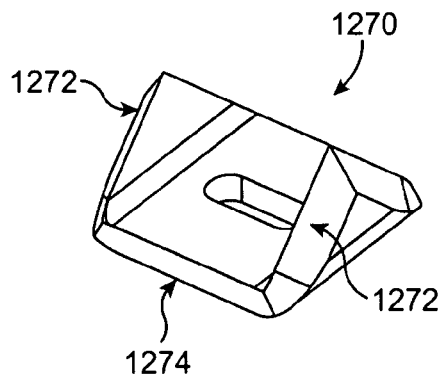
FIG. 29 is a perspective view of a double-blade member for attachment to a flexible portion of a tissue modification device, according to one embodiment of the present invention.

In FIG. 28E, much of the ligamentum flavum LF has been removed, and blades 1262, 1262' are in a position to treat bone. In some cases, a physician may choose to continue using device 1260 to remove bone, while in other cases a physician may wish to remove mostly or exclusively ligamentum flavum LF tissue. In various embodiments, the physician may determine when a desired amount of soft tissue and/or bone is removed by using tactile feedback from device 1260, by removing device 1260 to examine tissue trapped in device 1260, by radiographic visualization such as fluoroscopy, by use of one or more sizing probes or other instruments to gauge the size of the intervertebral foramen IF, or any combination of such methods.

When a desired amount of tissue has been removed, device 1260 may be removed from the patient to complete the procedure. As mentioned, in some embodiments, device 1260 may be used to remove only ligamentum flavum LF tissue and then removed from the patient to end the procedure. In alternative embodiments, device 1260 (or a differently configured device) may be used to remove both soft tissue and bone. In yet another alternative embodiment, a first device (for example, device 1260) may be used to remove ligamentum flavam LF tissue, the first device may be removed from the patient, and a second device may be inserted and used to remove bone. Thus, in some embodiments, two different devices may be used in one procedure, with one device optimized for soft tissue removal and another device optimized for bone removal.

With reference now to FIGS. 29-32, various embodiments of blade structures are shown. For example, in an embodiment as in FIG. 29, a blade structure 1270 may include two blades 1272 extending substantially vertically from a base 1274. Base 1274 may provide a surface for attaching blades 1272 to one side of a tissue modification device. Blades 1272 may have beveled cutting edges and pointed tips, as shown.

Figure 30:
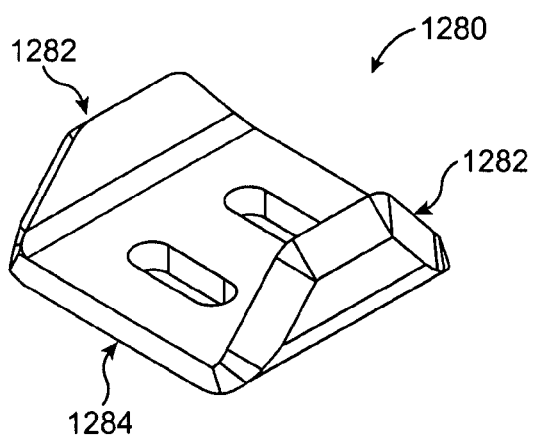
FIG. 30 is a perspective view of a double-blade member for attachment to a flexible portion of a tissue modification device, according to an alternative embodiment of the present invention.

In an alternative embodiment, as in FIG. 30, a blade structure 1280 may again include two blades 1282 extending vertically from a base 1284. In this embodiment, blades 1282 have beveled edges and a flat, beveled top.

Figure 31:
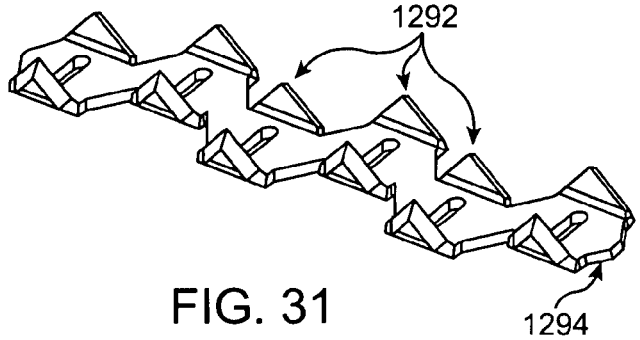
FIG. 31 is a perspective view of another embodiment of a blade structure.

In another alternative embodiment, as in FIG. 31, a blade structure 1290 may include any number of blades 1292 coupled with a base 1294. In this embodiment, twelve blades 1292 are coupled with base 1294, and base 1294 has a back-and-forth or zig-zag configuration.

Figure 32:
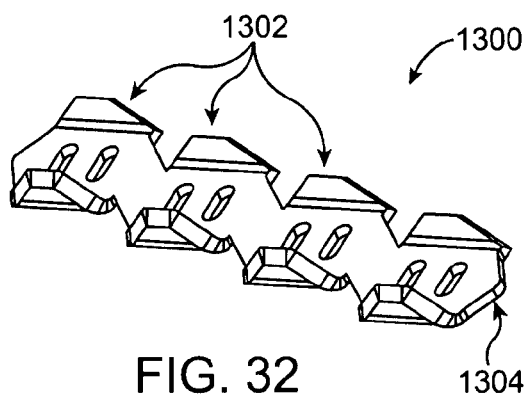
FIG. 32 is a perspective view of another embodiment of a blade structure.

In another alternative embodiment, as in FIG. 32, a blade structure 1300 may include eight, flat-top blades 1302 (or any other suitable number) coupled with a base 1304 having a diagonal configuration. When base 1304 is attached to a surface of a tissue modification device, blades 1302 will typically be angled due to the diagonal configuration of base 1304.

In various alternative embodiments, any of the tissue modification devices and method described above may be used in combination with one or more vertebral distraction devices. In one embodiment, for example, an interspinous implant such as the X STOP® implant (offered by St. Francis Medical Technologies, Inc., Alameda, Calif., www.sfmt.com) may be inserted between adjacent vertebrae, and then access devices and/or tissue removal devices described herein may be used to remove or otherwise modify spinal tissue. Such an implant may be inserted and left in place after a procedure, while in alternative embodiments a distraction device may be used only during a tissue removal procedure. Various embodiments and aspects of such distraction/tissue removal combinations are described in greater detail in U.S. Provisional Patent Application Ser. No. 60/884,371, titled "Spinal Stenosis Treatment Methods and Apparatus," filed Jan. 10, 2007, the full disclosure of which is hereby incorporated by reference.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A system for modifying tissue in a patient, the system comprising:
   a tissue modification device comprising:
      an elongate body having a proximal portion, and a flexible distal portion having opposing first and second major surfaces extending longitudinally;
      one or more tissue modifying members disposed along the first major surface, wherein the second major surface is an atraumatic surface; and
      a guidewire coupler near the distal end of the body configured to retain the proximal end of a guidewire relative to the guidewire coupler so that the tissue modification device may be pulled distally by pulling the guidewire distally and so that the tissue modification device may be released from the guidewire by pushing the guidewire proximally;
   a proximal handle configured to couple with the proximal portion of the tissue modification device;
   a guidewire configured to couple to the tissue modification device; and
   a distal handle configured to couple with the guidewire outside of the patient.

2. The system of claim 1, wherein the tissue modification device is configured to modify spinal tissue, and wherein the tissue modification device is configured to extend into the patient's body, along a curved path through an intervertebral foramen of the spine, and out of the patient's body, such that at least part of the flexible distal portion of the elongate body of the device extends into the intervertebral foramen, and the proximal and distal handles reside outside the patient.

3. The system of claim 2, wherein a height of the tissue modifying member(s) is greater than a thickness of a ligamentum flavum of the spine.

4. The system of claim 1, wherein the tissue modifying member(s) are selected from the group consisting of uni-directional blades, bi-directional blades, teeth, hooks, barbs, pieces of wire saw, wires, meshes, woven material, knitted material, braided material, planes, graters, raised bumps, other abrasive surfaces, other abrasive materials and deliverable substances adhered to or formed in the first major surface.

5. The system of claim 1, wherein the tissue modifying member(s) are fixedly attached to or formed in the first major surface.

6. The system of claim 1, wherein the tissue modifying member(s) are moveably attached to or formed in the first major surface, and wherein the tissue modification device further comprises an actuator coupled with the tissue modifying member(s) and extending to the proximal handle for actuating the tissue modifying member(s).

7. The system of claim 1, wherein the elongate body is at least partially hollow, wherein the distal portion is flatter than the proximal portion, and wherein the tissue modifying members comprise blades formed in the first major surface of the distal portion.

8. The system of claim 1, wherein the guidewire coupler comprises a cavity for containing a shaped tip of the guidewire, and wherein the guidewire comprises at least one shaped tip for fitting within the cavity.

9. The system of claim 1, further comprising a material disposed over a portion of the elongate body distal portion to provide the distal portion with smooth edges.

10. The system of claim 9, wherein the material comprises a polymeric cover disposed over the distal portion with one or more openings through which the tissue modifying member(s) protrude.

11. The system of claim 1, wherein the tissue modification device is further configured to collect tissue removed by the tissue modifying member(s).

12. The system of claim 1, further comprising a tissue collection chamber formed in or attached to the elongate body.

13. The system of claim 1, wherein the guidewire coupler is configured to releaseably couple to the guidewire.

14. The system of claim 1, wherein the guidewire coupler is configured to retain the proximal end of the guidewire relative to the guidewire coupler so that the tissue modification device may be urged against the tissue so that the tissue modification device forms a bend against the target tissue to modify the tissue by pulling on the proximal end of the elongate body while pulling distally on the guidewire.

15. A device for modifying tissue in a patient, the device comprising:
an elongate body comprising:
a rigid proximal portion;
a flexible distal portion; and
an intermediate flexible portion disposed between the proximal and distal portions and having opposing first and second major surfaces extending longitudinally;
one or more tissue modifying members disposed along the first major surface of the intermediate portion of the body but not the second major surface; and
a guidewire coupler near the distal end of the body configured to retain the proximal end of a guidewire relative to the guidewire coupler so that the tissue modification device may be pulled distally by pulling the guidewire distally and so that the tissue modification device may be released from the guidewire by pushing the guidewire proximally.

16. A device as in claim 15, wherein the device is configured to modify spinal tissue, and wherein the device is configured to extend into the patient's body, along a curved path through an intervertebral foramen of the spine, and out of the patient's body, such that at least part of the flexible intermediate portion of the elongate body of the device extends into the intervertebral foramen.

17. A device as in claim 15, wherein at least the proximal and intermediate portions of the elongate body are at least partially hollow, thus forming at least one lumen.

18. A device as in claim 17, wherein the at least one lumen comprises at least one of a suction lumen and an irrigation lumen.

19. A device as in claim 17, further including at least one tissue transport member slidably disposed within the lumen and configured to remove tissue out of the device.

20. A device as in claim 19, wherein the tissue transport member comprises one or more flexible wires having tissue collection portions disposed under the tissue modifying member(s) of the device.

21. A device as in claim 20, wherein the tissue collection portions are selected from the group consisting of shaped portions of the wire(s), adhesive coating(s) on the wire(s), tissue collecting material(s) on the wire(s) and adhesive material(s) used to make the wire(s) themselves.

22. A device as in claim 19, wherein the tissue transport member comprises a piece of tissue adhering material disposed under the tissue modifying member(s) of the device.

23. A device as in claim 19, wherein the tissue transport member comprises a removable tissue collection chamber disposed under the tissue modifying member(s) of the device.

24. A device as in claim 19, wherein the tissue transport member comprises at least one unidirectional valve for allowing tissue to pass through the shaft toward the proximal handle while preventing the cut tissue from passing through the valve(s) toward the tissue modifying member(s) of the device.

25. A device as in claim 15, wherein at least part of the elongate body is sufficiently flexible to be compressible, such that tissue may be moved through the elongate body by compressing the compressible portion.

26. A device as in claim 15, further comprising a tissue collection chamber formed in or attached to the elongate body.

27. The system of claim 15, wherein the guidewire coupler is configured to releaseably couple to the guidewire.

28. The system of claim 15, wherein the guidewire coupler is configured to retain the proximal end of the guidewire relative to the guidewire coupler so that the tissue modification device may be urged against the tissue so that the tissue modification device forms a bend against the target tissue to modify the tissue by pulling on the proximal end of the elongate body while pulling distally on the guidewire.

29. A kit for modifying tissue in a patient, the kit comprising:
a tissue modification device, comprising:
a rigid shaft having a proximal end and a distal end;
a flexible substrate extending from the distal end of the shaft;
a proximal handle coupled with the shaft at or near its proximal end;
one or more tissue modifying members disposed along one side of the substrate; and
a guidewire coupler disposed on the substrate configured to retain the proximal end of the guidewire relative to the guidewire coupler so that the tissue modification device may be pulled distally by pulling the guidewire distally and so that the tissue modification device may be released from the guidewire by pushing the guidewire proximally;
a guidewire configured to couple with the guidewire coupler; and
a distal handle removably couplable with the guidewire outside the patient.

30. A kit as in claim 29, wherein the tissue modification device and guidewire, coupled together, are configured to extend into the patient's body, along a curved path through an intervertebral foramen of the spine, and out of the patient's body, such that at least part of the flexible substrate extends into the intervertebral foramen, and the proximal and distal handles reside outside the patient.

31. A kit as in claim 29, further comprising at least one probe for passing the guidewire between target and non-target tissues in a patient.

32. A kit as in claim 31, wherein the probe comprises a needle.

33. A kit as in claim 31, wherein the probe comprises a curved, cannulated probe.

34. A kit as in claim 31, further comprising a flexible guide member for passing through the probe, wherein the guide member has an inner diameter selected to allow passage of the guidewire therethrough.

35. A kit as in claim 29, wherein the device further comprises a tissue collection chamber configured to collect tissue.

36. A kit as in claim 35, wherein the device further comprises tissue transport means configured to transport the collected tissue through the device.

37. A device for modifying tissue,
with a proximal handle at the substantially proximal end of the device with a flexible distal portion of the device configured for tissue modification, such that when the user simultaneously pulls on both the proximal and distal ends of the device the flexible portion of the device is pulled under tension against a target tissue with a rigid portion of the device between a handle and the flexible portion of the device with the flexible portion of the device containing tissue modification elements along a first surface that is opposite from an atraumatic second surface on the other side of the first surface with a guidewire coupler at the distal end of the flexible portion configured to retain the proximal end of the guidewire relative to the guidewire coupler so that the tissue modification device may be pulled distally by pulling the guidewire distally and so that the tissue modification device may be released from the guidewire by pushing the guidewire proximally.

38. A device as in claim 37, where the target tissue is spinal tissue in at least one of the central spinal canal, the lateral recess or the neural foramen.

39. A device as in claim 37, where each tissue modification element comprises at least one of a blade, an abrasive, a plane, a saw, a hook, a spike, an electrode, a hemostatic agent, an anti-inflammatory agent, or an analgesic.

40. A device as in claim 37, where the tissue modification elements are covered during insertion.

41. A device, as in claim 37, where the tissue modification elements are covered when not pulled under tension against target tissues.

42. A device, as in claim 37, where the tissue modification elements are covered by a portion of the device that moves with the flexible portion of the device.

43. A device, as in claim 37, where the tissue modification elements are covered by a portion of the device that moves independently of the flexible portion of the device.

44. A device, as in claim 37, where the tissue modification elements are sharp blades, extending at angles from the flexible portion of the device to which they are attached.

45. A system for removing a target tissue of a patient, the system comprising:
a distal elongate flexible portion having a first end and a second end with an axis therebetween, the flexible portion having a first surface extending along the axis and a second surface opposite the first surface, wherein the flexible portion is axially bendable in a first lateral orientation;
a proximal portion extendable from the flexible portion configured so that movement of the proximal portion can shift the first surface toward a target region of the target tissue; a tissue modifying member disposed along the first surface to effect removal of the target region of the target tissue, wherein the second surface comprises an atraumatic surface; and
a guidewire coupler at the distal end of the flexible portion configured to retain the proximal end of a guidewire relative to the guidewire coupler so that the tissue modification device may be pulled distally by pulling the guidewire distally and so that the tissue modification device may be released from the guidewire by pushing the guidewire proximally.

46. The system of claim 45, further comprising a handle configured to connect to the proximal portion so that tension can be applied to the first end by pulling the proximal portion manually from outside the patient so as to urge the first surface against the target tissue when the flexible member bends over the target tissue in the first orientation.

47. The system of claim 46, wherein the proximal portion couples the handle to the flexible portion such that applying torque to the handle outside the body portion rotates the flexible portion about the axis so as to shift an orientation of the first surface toward a target region of the target tissue when the system is deployed for use.

48. The system of claim 47, the target tissue having a convex surface defining an outward orientation and an inward orientation, wherein the first surface is bordered by first and second opposed edges, wherein the rotation of the shaft portion can counteract a tension-induced rolling of the flexible body portion about the axis when the first edge is inward of the second edge.

49. The system of claim 46, further comprising a distal handle configured to be coupled with a second end of the flexible portion such that the flexible portion can be manually tensioned by simultaneous pulling, from outside the patient, on the first and second, ends and can be axially moved along a curving path within the patient by relative movement between the handles, the curving path including the bend over the target tissues.

50. The system of claim 49, wherein the tissue modifying member comprises a plurality of axially oriented blades extending from the first surface, the handles configured for reciprocating the tissue modifying member along the curved path and against the target tissue by sequentially pulling on the first and second handles so that the cutting edges incise the target tissue.

* * * * *